United States Patent
Yamazaki et al.

(10) Patent No.: US 12,371,451 B2
(45) Date of Patent: *Jul. 29, 2025

(54) INORGANIC POROUS CARRIER AND METHOD FOR PRODUCING NUCLEIC ACIDS USING SAME

(71) Applicant: SUMITOMO CHEMICAL COMPANY, LIMITED, Chuo-ku (JP)

(72) Inventors: Kanako Yamazaki, Kurashiki (JP); Masaki Kitahara, Chuo-ku (JP); Takashi Hara, Osaka (JP); Takeshi Yoshioka, Osaka (JP)

(73) Assignee: SUMITOMO CHEMICAL COMPANY, LIMITED, Chuo-ku (JP)

(*) Notice: Subject to any disclaimer, the term of this patent is extended or adjusted under 35 U.S.C. 154(b) by 826 days.

This patent is subject to a terminal disclaimer.

(21) Appl. No.: 17/599,297

(22) PCT Filed: Feb. 28, 2020

(86) PCT No.: PCT/JP2020/008318
§ 371 (c)(1),
(2) Date: Sep. 28, 2021

(87) PCT Pub. No.: WO2020/202950
PCT Pub. Date: Oct. 8, 2020

(65) Prior Publication Data
US 2022/0153774 A1    May 19, 2022

(30) Foreign Application Priority Data
Mar. 29, 2019  (JP) ................. 2019-067994

(51) Int. Cl.
*C01B 33/14*    (2006.01)
*C07H 21/00*    (2006.01)

(52) U.S. Cl.
CPC ............. *C07H 21/00* (2013.01); *C01B 33/14* (2013.01); *C01P 2004/32* (2013.01); *C01P 2004/61* (2013.01); *C01P 2006/12* (2013.01); *C01P 2006/14* (2013.01)

(58) Field of Classification Search
None
See application file for complete search history.

(56) References Cited

U.S. PATENT DOCUMENTS

| | | |
|---|---|---|
| 6,508,860 B1 | 1/2003 | Kulkarni et al. |
| 6,995,259 B1 | 2/2006 | Vargeese et al. |
| 7,205,399 B1 | 4/2007 | Vargeese et al. |
| 7,777,023 B2 | 8/2010 | Vargeese et al. |
| 2002/0076832 A1* | 6/2002 | Pirrung ............ G01N 33/54353 436/518 |
| 2009/0005536 A1 | 1/2009 | Rothstein et al. |
| 2009/0326210 A1 | 12/2009 | Mori et al. |
| 2011/0065822 A1 | 3/2011 | Mori et al. |
| 2011/0092690 A1 | 4/2011 | Hayakawa et al. |
| 2014/0235435 A1 | 8/2014 | Miyahara et al. |
| 2016/0311847 A1 | 10/2016 | Maeta et al. |
| 2017/0002038 A1 | 1/2017 | Horie et al. |
| 2022/0193648 A1 | 6/2022 | Arimura et al. |

FOREIGN PATENT DOCUMENTS

| | | | |
|---|---|---|---|
| CA | 3052561 A1 * | 8/2018 | ............. A61K 31/00 |
| CN | 103906708 A | 7/2014 | |
| CN | 108176387 A | 6/2018 | |
| EP | 2 138 519 A1 | 12/2009 | |

(Continued)

OTHER PUBLICATIONS

Office Action issued Feb. 20, 2024, in corresponding Japanese Patent Application No. 2021-511251 (with English Translation), 9 pages.
Extended European Search Report issued Sep. 29, 2023 in European Patent Application No. 20785077.7, 11 pages.
Japanese Office Action issued Oct. 3, 2023 in Japanese Patent Application No. 2021-511251 (with unedited computer-generated English Translation), 7 pages.
Chinese Office Action issued Oct. 19, 2023 in Chinese Application 202080023931.7 (with unedited computer-generated English translation), 17 pages.
European Office Action issued May 15, 2024 in European Patent Application No. 20 785 077.7, 4 pages.
Chinese Office Action issued Jan. 11, 2024 in Chinese Patent Application No. 202080023931.7 (with English translation), 18 pages.

(Continued)

*Primary Examiner* — Traviss C McIntosh, III
(74) *Attorney, Agent, or Firm* — Oblon, McClelland, Maier & Neustadt, L.L.P.

(57) ABSTRACT

An inorganic porous carrier having pore distribution where a pore diameter is 0.04 μm or more, and including a linker of formula (1) [where a bond * represents a bond to an oxygen atom of a silanol group in an inorganic porous substance. $R^1$ and $R^2$ represent each independently an alkyl group containing 3 to 10 carbon atoms, or a phenyl group. L represents a single bond; an alkylene group containing 1 to 20 carbon atoms; or an alkylene group containing 2 to 20 carbon atoms containing —$CH_2$-Q-$CH_2$— group wherein any group Q selected from a group consisting of —O—, —NH—, —NH—CO—, and —NH—CO—NH— is inserted into at least one of —$CH_2$—$CH_2$— group constituting the alkylene group. A carbon atom of the methylene group bound to the group Q does not bond to another group Q at the same time.]; and a method for preparing nucleic acids using the same.

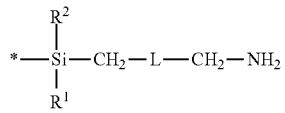

(1)

17 Claims, No Drawings

Specification includes a Sequence Listing.

(56) References Cited

FOREIGN PATENT DOCUMENTS

| | | | |
|---|---|---|---|
| EP | 2 298 820 A1 | 3/2011 | |
| EP | 2 772 466 A1 | 9/2014 | |
| EP | 3 106 519 A1 | 12/2016 | |
| EP | 3 950 127 A1 | 2/2022 | |
| JP | 3-23211 A | 1/1991 | |
| JP | 3-181334 A | 8/1991 | |
| JP | 2958338 B | 10/1999 | |
| JP | 2006-502856 A | 1/2006 | |
| JP | 2011-88843 A | 5/2011 | |
| JP | WO 2013/062105 A1 | 5/2013 | |
| WO | WO 2004/035170 A2 | 4/2004 | |
| WO | WO 2017/0119503 A1 | 7/2017 | |
| WO | WO-2017119503 A1 * | 7/2017 | ............. C12M 1/00 |
| WO | WO 2018/203574 A1 | 11/2018 | |
| WO | WO 2020/202952 A1 | 10/2020 | |

OTHER PUBLICATIONS

International Search Report issued May 19, 2020 in PCT/JP2020/008318 (submitting English translation only), 2 pages.

International Preliminary Report on Patentability and Written Opinion of the International Searching Authority issued Sep. 28, 2021 in PCT/JP2020/008318 (submitting English translation only), 7 pages.

International Search Report issued May 26, 2020 in PCT/JP2020/008313 (submitting English translation only), 3 pages.

International Preliminary Report on Patentability and Written Opinion of the International Searching Authority issued Sep. 28, 2021 in PCT/JP2020/008313 (submitting English translation only), 6 pages.

International Search Report issued May 19, 2020 in PCT/JP2020/008321 (submitting English translation only), 2 pages.

International Preliminary Report on Patentability and Written Opinion of the International Searching Authority issued Sep. 28, 2021 in PCT/JP2020/008321 (submitting English translation only), 7 pages.

International Search Report issued May 19, 2020 in PCT/JP2020/008323 (submitting English translation only), 2 pages.

International Preliminary Report on Patentability and Written Opinion of the International Searching Authority issued Sep. 28, 2021 in PCT/JP2020/008323 (submitting English translation only), 6 pages.

International Search Report issued May 19, 2020 in PCT/JP2020/008325 (submitting English translation only), 2 pages.

International Preliminary Report on Patentability and Written Opinion of the International Searching Authority issued Sep. 28, 2021 in PCT/JP2020/008325 (submitting English translation only), 6 pages.

J. Katzhendler, et al. "The Effect of Spacer, Linkage and Solid Support on the Synthesis of Oligonucleotides" Tetrahedron, vol. 45, No. 9, 1989, pp. 2777-2792.

Kiyohisa Imada, et al., "Studies on the Internal Surface of Porous Glass and Chemical Modification thereof" Journal of the Chemical Society of Japan, vol. 4, 1990, pp. 407-414 (with English translation).

Glenn Tong, et al., The Synthesis of Oligonucleotide-Polyamide Conjugate Molecules Suitable as PCR Primers, Journal of Organic Chemistry, vol. 58, No. 8, 1993, pp. 2223-2231.

J-Y. Wang, et al., "Preparation of a New Support for Solid Phase Synthesis of Glass Bead Surface with Amino" Hecheng Huaxue, Chinese Journal of Synthetic Chemistry, vol. 21, No. 1, 2013, pp. 66-69 (with English Abstract).

Roxana S. Timofte, et al., "Preparation of Silane-Grafted Pellets: Silica Bound Reagents in a Very Convenient Form" Tetrahedron Letters, vol. 45, 2004, pp. 39-42.

Combined Chinese Office Action and Search Report issued Mar. 30, 2023, in corresponding Chinese Patent Application No. 202080023931.7 (with English Translation), 21 pages.

U.S. Appl. No. 17/599,409, filed Sep. 28, 2021, Takuya Miyagawa, et al.

U.S. Appl. No. 17/599,787, filed Sep. 29, 2021, Masaki Kitahara, et al.

U.S. Appl. No. 17/599,700, filed Sep. 29, 2021, Takashi Arimura, et al.

U.S. Appl. No. 17/599,249, filed Sep. 28, 2021, Syusaku Hara, et al.

* cited by examiner

```
                        SEQUENCE LISTING

<160> NUMBER OF SEQ ID NOS: 3

<210> SEQ ID NO 1
<211> LENGTH: 23
<212> TYPE: RNA
<213> ORGANISM: Artificial Sequence
<220> FEATURE:
<223> OTHER INFORMATION: Synthesized RNA

<400> SEQUENCE: 1
gcagaguaca cacagcauau acc                                            23

<210> SEQ ID NO 2
<211> LENGTH: 25
<212> TYPE: RNA
<213> ORGANISM: Artificial Sequence
<220> FEATURE:
<223> OTHER INFORMATION: Synthesized RNA

<400> SEQUENCE: 2
```

```
gguauaugcu guguguacuc ugcuu                                      25

<210> SEQ ID NO 3
<211> LENGTH: 103
<212> TYPE: RNA
<213> ORGANISM: Artificial Sequence
<220> FEATURE:
<223> OTHER INFORMATION: Syntesized RNA

<400> SEQUENCE: 3
auaacucaau uuguaaaaaa guuuuagagc uagaaauagc aaguuaaaau aaggcuaguc   60
cguuaucaac uugaaaaagu ggcaccgagu cggugcuuuu uuu                   103
```

INORGANIC POROUS CARRIER AND METHOD FOR PRODUCING NUCLEIC ACIDS USING SAME

CROSS-REFERENCE TO RELATED APPLICATIONS

The present application is a 35 U.S.C. § 371 national stage patent application of International patent application PCT/JP2020/008318, filed on Feb. 28, 2020, which is based on and claims the benefits of priority to Japanese Application No. 2019-067994, filed on Mar. 29, 2019. The entire contents of these applications are incorporated herein by reference.

TECHNICAL FIELD

This application claims priority to and the benefit of Japanese Patent Application No. 2019-067994 filed on Mar. 29, 2019, the entire contents of which are incorporated herein by reference.

The present invention relates to an inorganic porous carrier, and a method for preparing a nucleic acid using the same, as well as a silane coupling agent suitable for introducing a functional group into an inorganic porous substance.

BACKGROUND ART

As a chemical synthesis method of a nucleic acid, a solid-phase synthesis method by a phosphoramidite method has been widely used. In this method, first, a functional group such as an amino group is introduced onto an inorganic porous substance by a silane coupling agent or the like, and a nucleoside providing a 3'end of the nucleic acid is bound to the functional group. Then, a nucleic acid elongation reaction is carried out on the solid-phase carrier starting from the nucleoside.

In the solid-phase synthesis method, when a strand length of the nucleic acid to be synthesized becomes long, a synthesis efficiency drastically decreases, and consequently, a large amount of by-products is prone to be produced and mixed. It is considered that this is because the nucleic acid molecules that elongates on the surface of the solid-phase carrier interfere with each other, resulting in inhibition of elongation reaction inhibitions, occurrence of side reactions, or the like.

As a technique for preventing interference between nucleic acid molecules on the surface of the solid-phase carrier, for example, it has been proposed to lengthen a spacer of an alkylamino group introduced onto the carrier (see Non-Patent Document 1).

CITATION LIST

Non-Patent Document

Non-Patent Document 1: J. Katzendler et al., Tetrahedron, 45, 2777, 1989

SUMMARY OF THE INVENTION

Problems to be Solved by Invention

Generally, as a nucleic acid to be synthesized becomes longer, an influence of interference between nucleic acid molecules would be greater. Accordingly, in the conventional solid-phase synthesis method, the yield and purity in the nucleic acid synthesis have a tendency to decrease.

The present invention has been made in view of the above situation, and the problem to be solved by the present invention is to provide an inorganic porous carrier which can improve the yield etc. in the preparation of nucleic acid, and a method for preparing a nucleic acid using the same.

Means to Solve Problems

In order to solve the above problem, the present invention adopts the following constituents.

That is, a first aspect of the present invention is directed to an inorganic porous carrier which comprises a linker represented by the following general formula (1) and has a pore distribution in which a pore size (mode diameter, the same shall apply hereinafter) is 0.04 μm or more:

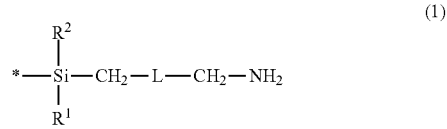

(1)

[wherein, a bond marked with * represents a bond to an oxygen atom of a silanol group in an inorganic porous substance;

$R^1$ and $R^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom; and L represents a single bond; an alkylene group containing 1 to 20 carbon atoms; or an alkylene group containing 2 to 20 carbon atoms which contains —$CH_2$-Q-$CH_2$— group wherein any group Q selected from a group consisting of —O—, —NH—, —NH—CO— and —NH—CO—NH— is inserted into at least one of —$CH_2$—$CH_2$— group constituting the alkylene group; providing that a carbon atom of the methylene group bound to the group Q does not bond to another group Q at the same time].

A second aspect of the present invention is directed to an inorganic porous carrier which comprises a linker represented by the following general formula (2) and has a pore distribution in which a pore size (mode diameter) is 0.04 μm or more (hereinafter, this inorganic porous carrier may be referred to as "Solid-phase carrier"):

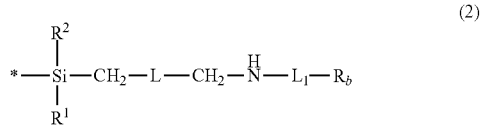

(2)

[wherein, a bond marked with * represents a bond to an oxygen atom of a silanol group in an inorganic porous substance;

$R^1$ and $R^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom;

L represents a single bond; an alkylene group containing 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of the methylene group bound to the group Q does not bond to another group Q at the same time;

$R_b$ represents a nucleoside or nucleotide in which a reactive group is protected or deprotected; and $L_1$ represents a divalent group bound to an oxygen atom of a primary or secondary hydroxyl group in $R_b$.]
(hereinafter, the inorganic porous carrier according to the first aspect and the inorganic porous carrier according to the second aspect are collectively referred to as "Inorganic porous carrier of the present invention" or "Present inorganic porous carrier").

In one embodiment according to the second aspect of the present invention, $L_1$ in the general formula (2) may represent a succinyl linker or a universal linker.

In one embodiment according to the first or second aspect of the present invention, a surface area per volume of the inorganic porous substance may be within a range of 0.1 m$^2$/mL or more and 100 m$^2$/mL or less.

In one embodiment according to the first or second aspect of the present invention, a pore volume per volume of the inorganic porous substance may be within a range of 0.05 mL/mL or more and 0.6 mL/mL or less.

In one embodiment according to the first or second aspect of the present invention, a porosity of the inorganic porous substance may be 50% or more.

In one embodiment according to the second aspect of the present invention, a density of the grafted linker may be within a range of 0.1 μmol/m$^2$ or more and 5.0 μmol/m$^2$ or less with respect to a specific surface area per mass of the inorganic porous substance.

In one embodiment according to the first or second aspect of the present invention, a particle size (median diameter) of the inorganic porous substance may be within a range of 1 μm or more and 1000 μm or less.

In one embodiment according to the first or second aspect of the present invention, the inorganic porous substance may be silica, silica gel, zeolite, or glass.

A third aspect of the present invention is directed to a method for preparing a nucleic acid, which is carried out using the inorganic porous carrier wherein $R_b$ in the general formula (2) represents a nucleoside or nucleotide in which a hydroxyl group as a reactive group is protected, wherein the method comprises the following steps:

a step (A) of deprotecting a protecting group of the hydroxyl group at a 5'position of the nucleoside;

a step (B) of subjecting the hydroxyl group at the 5'position of the nucleoside produced in the step (A) to a condensation reaction with an amidite compound having a second nucleoside base to produce a phosphite;

a step (C) of oxidizing the phosphite produced in the step (B) to produce a nucleotide; and a step (D) of deprotecting a protecting group of a hydroxyl group at a 5'position of the nucleotide produced in the step (C) (hereinafter, referred to as "Method for preparing a nucleic acid of the present invention").

In one embodiment according to the third aspect of the present invention, the method for preparing nucleic acid may further comprise the following steps:

a step (B') of subjecting the product produced in the step (D) to a condensation reaction with an amidite compound having a nucleoside base to be introduced in next time to produce a phosphite;

a step (C') of oxidizing the phosphite produced in the step (B') to produce an oligonucleotide; and a step (D') of deprotecting a protecting group of a hydroxyl group at a 5'position in an end of an oligonucleotide strand produced in the step (C').

In one embodiment according to the third aspect of the present invention, the method for preparing nucleic acid may further comprise a step (E) of carrying out a series of steps consisting of the above step (B'), step (C') and step (D') repeatedly m times (wherein m is an integer of 1 or more) to react the number of m of amidite compounds, and then cleaving an elongated nucleic acid.

A fourth aspect of the present invention is directed to a silane coupling agent which is represented by the following general formula (3):
(hereinafter, referred to as "Silane coupling agent of the present invention" or "Present silane coupling agent").

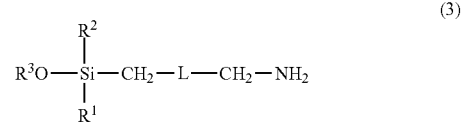

[wherein, $R^1$ and $R^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom;

L represents a single bond; an alkylene group containing 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of the methylene group bound to the group Q does not bond to another group Q at the same time;

$R^3$ represents a hydrogen atom or an alkyl group containing 1 to 4 carbon atoms; and providing that the following compounds are excluded: a compound wherein L represents a methylene group, $R^1$ represents an isopropyl group, $R^2$ represents an isopropyl group and $R^3$ represents an ethyl group, and a compound wherein L represents a methylene group, $R^1$ represents a n-propyl group, $R^2$ represents a n-propyl group and $R^3$ represents a n-propyl group].

A fifth aspect of the present invention is directed to a use of the inorganic porous carrier according to the first aspect or the solid-phase carrier according to the second aspect in a preparation of nucleic acid by a phosphoramidite method.

Effect of Invention

The inorganic porous carrier according to the present invention can further improve the purity or yield in the preparation of nucleic acid.

The method for preparing nucleic acid according to the present invention can further improve the purity or yield, and particularly obtain a long-stranded nucleic acid in high yield.

MODE FOR CARRYING OUT THE INVENTION

As used herein, when a certain numerical range is referred to as "A to B" or "A-B", it means a range represented by "from A or more to B or less" unless otherwise stated.
(Inorganic Porous Carrier)

The inorganic porous carrier according to the first aspect of the present invention is described below.

The inorganic porous substance constituting the inorganic porous carrier of the present embodiment is an inorganic porous substance which has a pore distribution in which a pore size is 0.04 μm or more, and typically an inorganic porous substance having a silanol group which can support a silane coupling agent. Examples of such an inorganic porous substance typically include silica, silica gel, zeolite, glass, quartz, or a mixture of two or more thereof, and preferably include silica, silica gel, zeolite, or glass. As the above inorganic porous substance, commercially available products may be used, or a substance prepared by a synthesis method as described below may be used.

[Method for Preparing Inorganic Porous Substance Containing Silanol Groups]

Examples of the method for preparing the inorganic porous substance containing the silanol groups include a dry method and a wet method. Specific examples of the former include a combustion method and an arc method, and specific examples of the latter include synthesis methods such as a precipitation method, a sol-gel method, and a hydrothermal synthesis method (Reference: TOSOH Research & Technology Review Vol. 45 (2001).).

The preparation of such an inorganic porous substance is carried out by, for example, using silicate, alkoxysilane, chlorosilane or the like as raw materials according to the synthesis method as described above using a solvent and a template.

The preparation of the inorganic porous substance can be carried out, for example, according to any one of the following methods: 1. a method of precipitating silica, and then removing a solvent contained in a framework of the silica; 2. a method of precipitating a solid after mixing silica with dissimilar metal other than silica such as aluminum, boron, or the like, and then phase-separating the resulting mixture into a silica component and a component other than silica, and removing the component other than silica; 3. a method of precipitating silica after mixing silica with an ammonium salt or a polymer as a template agent, and then removing the template agent; and 4. a method of aggregating a precipitated silica. A combination of two or more of the above methods may be used.

The methods of removing the solvent or the template agent in the above methods 1 and 3 may include drying, supercritical extraction, calcining or the like.

The inorganic porous substance to be obtained is preferably in a form of particles, and may be formed into a spherical shape, or may be formed into a massive shape or a crushed shape, whereas, when they are used as carriers, the spherical shape or the crushed shape is preferable from the viewpoint of filling into a column for nucleic acid synthesis.

The forming method is not particularly limited, but a spray drying method or an emulsion method may be used.

A size of the inorganic porous substance is not particularly limited, but from the viewpoint of column filling efficiency in the solid-phase synthesis of nucleic acid, and liquid feeding rate in a column filling, and the like, a particle size (median diameter, the same shall apply hereinafter) which is measured by a laser diffraction method (scattering method) is preferably within a range of 1 to 1000 μm, more preferably 5 to 500 μm, and further more preferably 10 to 300 μm.

A porous substance having a pore size of 0.04 μm or more is used as the inorganic porous substance according to the present embodiment. The inorganic porous substance to be used can be appropriately selected depending on the strand length of the nucleic acid to be synthesized. In general, when a strand length of the nucleic acid to be synthesized becomes long, it is preferable to select the inorganic porous substance having a large pore size. For example, when RNA of 40-mer to 200-mer is synthesized, the pore size is preferably within a range of 0.04 μm or more and 0.5 μm or less, and more preferably within a range of 0.04 μm or more and 0.3 μm or less.

The pore size (mode diameter) is determined based on a value of X-axis at a peak top in the pore size distribution obtained by the mercury intrusion method (a graph in which the X-axis is a value of the pore size and the Y-axis is a value obtained by calculating differentially the pore volume by the pore size).

The surface area per volume of the inorganic porous substance as described above is not particularly limited. In order to improve a productivity of nucleic acid per column, it is preferable that the surface area per volume of the inorganic porous substance is large regardless of the strand length of the nucleic acid. Specifically, the surface area per volume of the inorganic porous substance is preferably within a range of 0.1 to 100 $m^2/mL$, more preferably 1 to 50 $m^2/mL$, and further more preferably 3 to 20 $m^2/mL$.

The surface area per volume of the inorganic porous substance is determined by multiplying the bulk density (g/mL), which is measured by the mercury intrusion method, by the specific surface area per mass of the inorganic porous substance ($m^2/g$), which is measured by $N_2$ adsorption/desorption isotherm measurement. Here, as the specific surface area per mass as described above, a value obtained from an average gradient in a range of αs=1.7 to 2.1 according to a method such as a αs-plot method is used.

The pore volume of the inorganic porous substance of the present embodiment is not particularly limited. Generally, in order to improve the productivity of nucleic acid per column, it is preferable that the pore volume per volume of the inorganic porous substance (mL/mL) is high regardless of the strand length of the nucleic acid. The pore volume per volume of the inorganic porous substance is preferably within a range of 0.05 to 0.6 mL/mL, and more preferably 0.05 to 0.5 mL/mL.

The pore volume per volume of the inorganic porous substance is determined by multiplying the bulk density (g/mL), which is measured by the mercury intrusion method, by the cumulative pore volume (mL/g) of pore having a pore size within a range of 0.04 μm to 1 μm.

The porosity of the inorganic porous substance is not particularly limited, and generally, in order to improve the productivity of nucleic acid per column, it is preferable that the porosity is high regardless of the strand length of the nucleic acid. The porosity is determined by the mercury intrusion method, and it is preferably 50% or more, and more preferably 70% or more.

The porosity herein is calculated based on the pore volume of pore having a pore size within a range of 0.004 to 200 μm, which is a range measured by the mercury intrusion method. That is, it is determined by multiplying the cumulative pore volume (mL/g) of pore having a pore size within the range of 0.004 μm to 200 μm by the bulk density (g/mL).

The inorganic porous carrier of the present embodiment contains a linker represented by the following general formula (1):

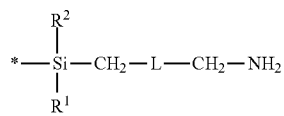

(1)

[wherein, a bond marked with * represents a bond to an oxygen atom of a silanol group in an inorganic porous substance;

R$^1$ and R$^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom; and L represents a single bond; an alkylene group containing 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of the methylene group bound to the group Q does not bond to another group Q at the same time.]

In the formula (1), the alkyl group in each of R$^1$ and R$^2$ may be any of a linear alkyl group, a branched alkyl group or a cyclic alkyl group, and preferably a branched alkyl group so as to improve the yield easily. The alkyl group in each of R$^1$ and R$^2$ contains 3 to 10 carbon atoms, preferably 3 to 6 carbon atoms, and more preferably 3 or 4 carbon atoms.

Examples of the alkyl group in each of R$^1$ and R$^2$ include a linear alkyl group such as n-propyl group, n-butyl group, n-hexyl group and n-octyl group; a branched alkyl group such as isopropyl group, isobutyl group, sec-butyl group, tert-butyl group, 2-ethylhexyl group and 3,7-dimethyloctyl group; and a cyclic alkyl group such as cyclopropyl group and cyclohexyl group.

The substituent which may be optionally substituted on the alkyl group represented by each of R$^1$ and R$^2$ is an alkoxy group or a fluorine atom. Examples of the alkoxy group include an alkoxy group containing 1 to 3 carbon atoms.

The substituent which may be optionally substituted on the phenyl group represented by each of R$^1$ and R$^2$ is an alkyl group, an alkoxy group, or a fluorine atom. Examples of the alkyl group include an alkyl group containing 1 to 5 carbon atoms. Examples of the alkoxy group include an alkoxy group containing 1 to 3 carbon atoms.

R$^1$ and R$^2$ may be identical to or different from each other, and preferably identical to each other from the viewpoint of synthesis (for example, convenience and efficiency).

In the formula (1), the alkylene group containing 1 to 20 carbon atoms in L may be any of a linear alkylene group or a branched alkylene group, and preferably a linear alkylene group so as to improve the yield easily. The alkylene group in L contains 1 to 20 carbon atoms, preferably 1 to 10 carbon atoms, and more preferably 1 to 6 carbon atoms.

Further, in the formula (1), L may represent an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group. However, a carbon atom of the methylene group bound to the group Q does not bond to another group Q at the same time.

[Method for Preparing Inorganic Porous Substance Supporting Linker (Inorganic Porous Carrier)]

The inorganic porous carrier of the present embodiment can be prepared, for example, by a method of treating a surface of the inorganic porous substance with a silane coupling agent represented by the following general formula (3a):

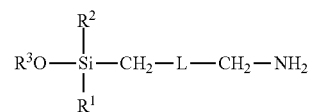

(3a)

[wherein, R$^1$ and R$^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom;

L represents a single bond; an alkylene group containing 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of the methylene group bound to the group Q does not bond to another group Q at the same time; and R$^3$ represents a hydrogen atom or an alkyl group containing 1 to 4 carbon atoms.]

In the formula (3a), R$^1$, R$^2$ and L can be described in the same manner as the description of R$^1$, R$^2$ and L in the formula (1).

In the formula (3a), the alkyl group in R$^3$ is preferably an alkyl group containing 1 to 3 carbon atoms, and more preferably a methyl group or an ethyl group.

Specific examples of the silane coupling agent represented by the general formula (3a) preferably include the followings.

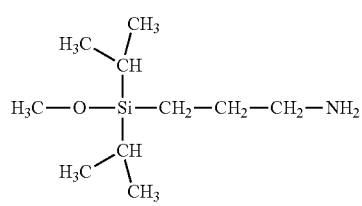

(3a-1)

(3a-2)
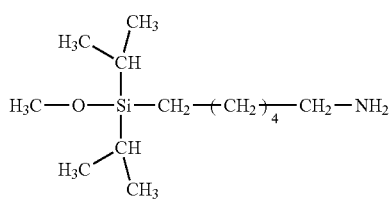
(3a-3)
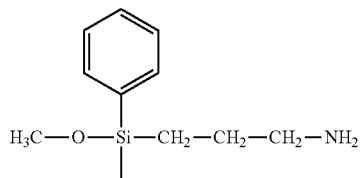
(3a-4)
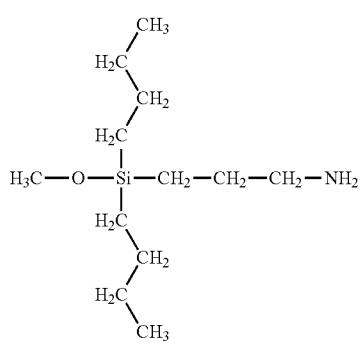
(3a-5)
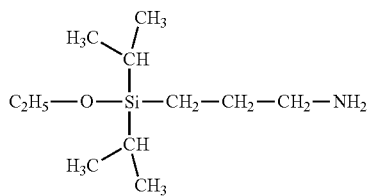
(3a-6)
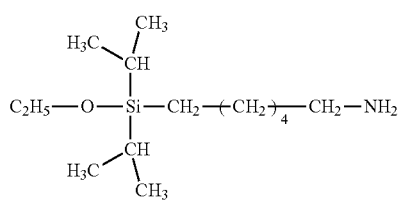
(3a-7)
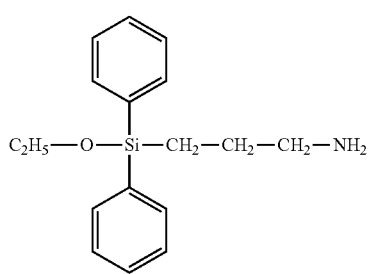
(3a-8)
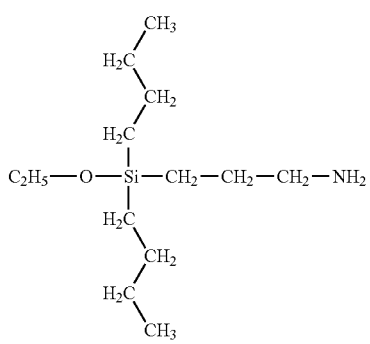
(3a-9)
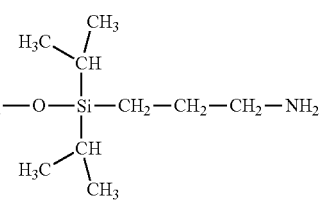
(3a-10)
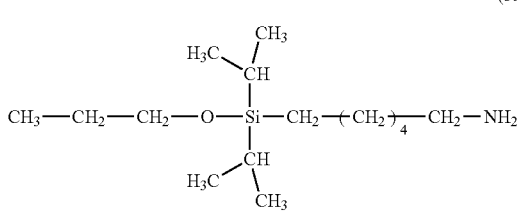
(3a-11)
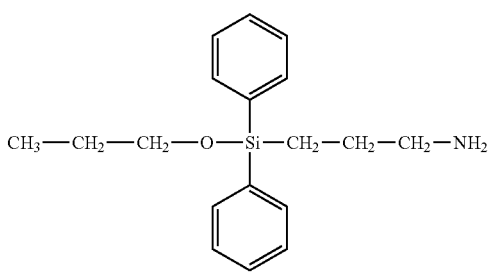
(3a-12)
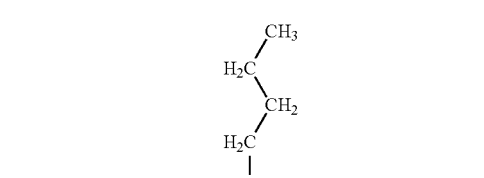
(3a-13)
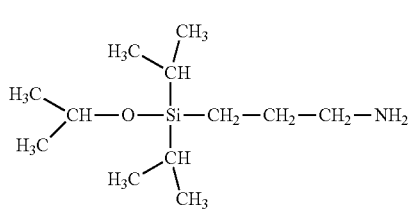

-continued
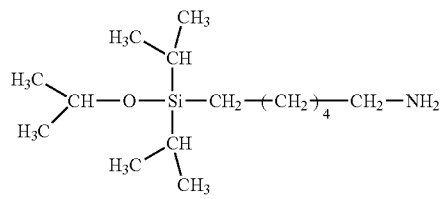
(3a-14)
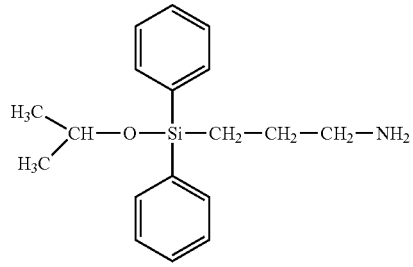
(3a-15)
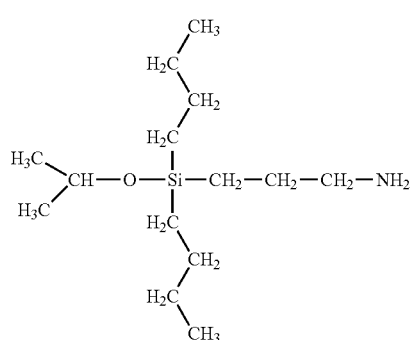
(3a-16)
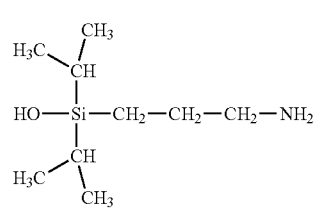
(3a-17)
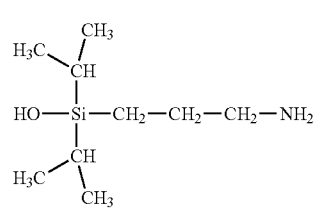
(3a-18)
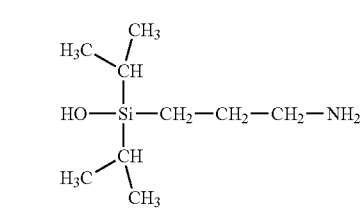
(3a-19)
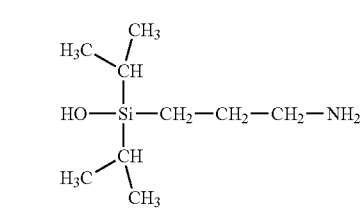
(3a-20)
The silane coupling agent represented by the above general formula (3a) can be prepared through the reaction route as shown below (synthetic route 1, synthetic route 2, or synthetic route 3).
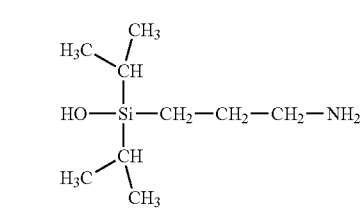

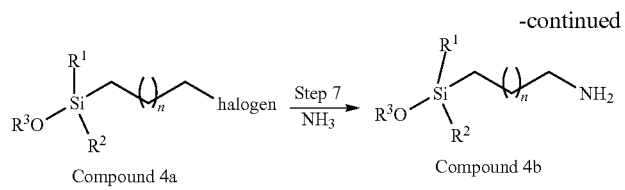

Details of synthetic route 1 (Step1→Step2→Step3):

For example, when compound 1 is trichlorosilane, the compound 1 is reacted with an organolithium compound or an organomagnesium compound corresponding to each of $R^1$ and $R^2$ (nucleophilic substitution reaction) to obtain compound 2 (Step 1). Then, the compound 2 is reacted with $R^3OH$ (for example, methanol, ethanol, propanol, etc.) in the presence of a base, or is reacted with an alcoholate such as $R^3ONa$ or water ($R^3$: hydrogen) to obtain silane compound 3 (Step 2). Then, the compound 3 is subjected to a hydrosilylation reaction with an amine compound or a halogen compound containing a terminal olefin (for example, allylamine or 6-chloro-1-hexene) in the presence of a platinum catalyst to synthesize silane compound 4 (Step 3).

Alternatively, when compound 1 is an alkoxysilane (for example, trimethoxysilane, triethoxysilane, etc.), substituents ($R^1$, $R^2$) may be introduced into the compound 1 by a nucleophilic substitution reaction according to the same reaction as described above, and then the resulting compound may be subjected to the hydrosilylation reaction to synthesize the silane compound 4.

Details of synthetic route 2 (Step4→Step5→Step6):

For example, when compound 1 is trichlorosilane, the compound 1 is subjected to a hydrosilylation reaction in the presence of a platinum catalyst, and accordingly a strand providing a spacer is attached thereto to obtain compound 5 (Step 4). Then, the substituents ($R^1$, $R^2$) as described above are introduced thereto by a nucleophilic substitution reaction to obtain compound 6 (Step 5). Then, the compound 6 is reacted with $R^3OH$ (for example, methanol, ethanol, propanol, etc.) in the presence of a base, or is reacted with an alcoholate such as $R^3ONa$ or water ($R^3$: hydrogen) to obtain the silane compound 4 (Step 6).

The introduction of $R^3O$ group (methoxy group, ethoxy group, propoxy group, etc.) in each of Step 2 and Step 6 can be carried out by a method of adding methanol, ethanol, propanol, or the like as the reagent $R^3OH$ to a solution containing the compound 2 or the compound 6; or a method of adding the compound 2 or the compound 6 dropwise to the corresponding alcohol or a solution containing the corresponding alcohol.

Details of Synthetic Route 3 (Step 7):

In the above-mentioned synthetic route 1 and synthetic route 2, the silane compound 4 which contains a functional group Y (an amino group or a halogen atom) may be obtained.

When the functional group Y is an amino group, various silane coupling agents can be prepared by a method of carbamoylation, amidation or ureidation of the amino group of the silane compound 4.

When the functional group Y is a halogen atom, the silane compound 4a is reacted with an ammonia or a primary amine compound, and accordingly the halogen atom is eliminated, and an amino group or an imino group (—NH—) is introduced thereto to obtain silane compound 4b. Various silane coupling agents can be prepared as itself or by the same method as described above (Step 7).

It is preferable to use a reaction solvent in any of the above-mentioned reactions. The reaction solvent is preferably an organic solvent such as pentane, hexane, heptane, toluene, tetrahydrofuran, or the like, or a mixture of two or more thereof.

The silane compound is usually purified by distillation under normal pressure or reduced pressure conditions. The obtained silane coupling agent is purified by, for example, liquid separation, distillation, or column chromatography.

The preparation of the inorganic porous carrier containing the linker represented by the general formula (1) is carried out, for example, by a method of mixing the inorganic porous substance with a certain silane coupling agent and a solvent, and then removing the solvent. In this case, the certain silane coupling agent is covalently bound to a silanol group on the surface of the inorganic porous substance by the mixing to form an inorganic porous carrier supporting the linker represented by the general formula (1).

Examples of the solvent as described above include acetonitrile, toluene, anisole, 2-heptanone, propyleneglycol monomethyl ether acetate, N,N-dimethylformamide, tetrahydrofuran, pentane, hexane, heptane, xylene, mesitylene, dichloromethane, chlorobenzene, water and the like, or a mixture of two or more thereof, and preferably include toluene.

The above-mentioned inorganic porous substance and solvent are preferably used after being dehydrated from the viewpoint of suppressing a polymerization of the silane coupling agent as itself and facilitating the reaction of the silane coupling agent with the surface of the inorganic porous substance. The dehydration method is not particularly limited, but examples thereof include a method of heating the inorganic porous substance under reduced pressure; and a method of dispersing the inorganic porous substance in the solvent and then distilling off the solvent under normal pressure or reduced pressure to conduct an azeotrope dehydration.

When the inorganic porous substance is mixed with the silane coupling agent and the solvent, the mixture is usually heated to near the boiling point of the solvent to facilitate the reaction, but the temperature is not limited thereto, and the mixture may be mixed at room temperature, or in a state where it is cooled to room temperature or less.

The reaction of the inorganic porous substance with the silane coupling agent is usually carried out for about 1 to 12 hours, but in the case that the silane coupling agent containing an amino group is used, since the silane coupling agent as itself has a catalytic effect of facilitating the reaction, the reaction may be carried out for about a several minutes.

An amount of the silane coupling agent to be added is usually an amount in which a density of the grafted linker is within a range of 0.1 to 5.0 µmol/m², and preferably 0.5 to 2.0 µmol/m², with respect to the specific surface area per mass of the inorganic porous substance, which is determined by $N_2$ adsorption/desorption measurement.

The silanol group which is not used in the reaction with the silane coupling agent, if needed, may be capped with a functional group which is inert to the nucleic acid synthesis, for example, trimethylsilyl group.

As described above, the surface of the inorganic porous substance can be treated with a certain silane coupling agent to produce the inorganic porous carrier which is modified with an aminosilyl group containing substituents ($R^1$, $R^2$).

(Method for Preparing Nucleic Acid)

In the method for preparing nucleic acid of the present embodiment, the nucleic acid can be synthesized with the above-mentioned inorganic porous carrier according to a publicly known method. Particularly, the preparation of nucleic acid is preferably carried out according to the phosphoramidite method. The nucleic acid synthesis method according to the phosphoramidite method is described below.

[Preparation of Solid-Phase Carrier]

A solid-phase carrier refers to a carrier wherein a nucleoside or nucleotide in which a reactive group is protected or deprotected is bound to the amino group (—$NH_2$) contained in the above-mentioned inorganic porous carrier through a divalent group.

In the present embodiment, the inorganic porous carrier which contains a linker represented by the following general formula (2) and has a pore distribution in which a pore size (mode diameter) is 0.04 μm or more can be used as the solid-phase carrier.

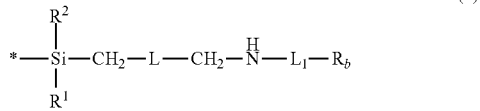

(2)

[wherein, a bond marked with * represents a bond to an oxygen atom of a silanol group in an inorganic porous substance;

$R^1$ and $R^2$ represent each independently an alkyl group containing 3 to 10 carbon atoms which may optionally have a substituent selected from a group consisting of an alkoxy group and a fluorine atom; or a phenyl group which may optionally have a substituent selected from a group consisting of an alkyl group, an alkoxy group and a fluorine atom;

L represents a single bond; an alkylene group containing 1 to 20 carbon atoms; or an alkylene group containing 2 to 20 carbon atoms which contains —$CH_2$-Q-$CH_2$— group wherein any group Q selected from a group consisting of —O—, —NH—, —NH—CO— and —NH—CO—NH— is inserted into at least one of —$CH_2$—$CH_2$— group constituting the alkylene group; providing that a carbon atom of the methylene group bound to the group Q does not bond to another group Q at the same time;

$R_b$ represents a nucleoside or nucleotide in which a reactive group is protected or deprotected; and $L_1$ represents a divalent group bound to an oxygen atom of a primary or secondary hydroxyl group in $R_b$.]

In the formula (2), $R^1$, $R^2$ and L are described in the same manner as the description of $R^1$, $R^2$ and L in the formula (1).

In the formula (2), the divalent group $L_1$ bound to the imino group (—NH—) preferably contains a succinyl group as a functional group.

Examples of the divalent group $L_1$ typically include a succinyl linker, a universal linker, and a linking group which is composed of a universal linker and a group linking an imino group (—NH—) in the formula (2) to the universal linker.

The universal linker contains a functional group (typically, a hydroxyl group) which can form a phosphite with the hydroxyl group of the nucleotide that provides a starting point of nucleic acid synthesis, and a functional group which can bond to an amino group at the end of linker represented by the formula (1), and further contains an adjacent protected functional group (for example, a protected amino group, a protected hydroxyl group, or a protected thiol group) in the same molecule, which can nucleophilically attack a phosphorus atom of phosphoric acid under the conditions for cleaving the synthesized nucleic acid.

More specifically, examples of the divalent group $L_1$ include a linking group represented by the following formula $L_{10}$, and a linking group represented by the following formula $L_{11}$.

$L_1$:

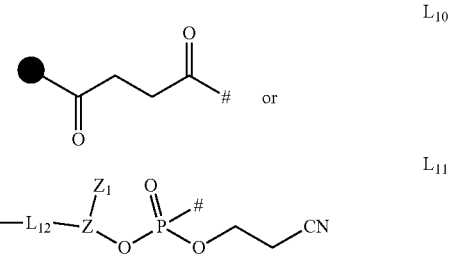

Here, in each of the formulae $L_{10}$ and $L_{11}$, the bond marked with • represents a bond to the imino group (—NH—) in the formula (2). The bond marked with # represents a bond to an oxygen atom of a primary or secondary hydroxyl group of $R_b$ in the above formula (2).

In the formula $L_{11}$, $Z_1$ represents a protected amino group, a protected hydroxyl group, or a protected thiol group. The oxygen atom and $Z_1$ which are bound to Z represent groups which are adjacent to each other (for example, they exist in vicinal position, and carbon atoms of Z that are attached thereto are directly bound to each other).

$L_{12}$ represents a group which links the imino group (—NH—) to the universal linker (for example, represented by •—$CO(CH_2)_2CO$-&; and the bond marked with & represents a bond to Z).

When the universal linker is used, even though the 3'end of the nucleic acid to be synthesized becomes any kinds of nucleoside or nucleotide, the nucleoside phosphoramidite providing the 3' end can be reacted and introduced in the same manner as the process of elongating the nucleic acid according to the usual nucleic acid automatic synthesis. Examples of such a universal linker include the compounds described in the following references, but are not limited thereto:

Reference: A. P. Guzaev, and M. Manoharan, J AmChem Soc, 2003, 125, 2380-2381.

Reference: R. K. Kumar, A. P. Guzaev, C. Rentel, and V. T. Ravikumar, Tetrahedron, 2006, 62, 4528.

In the formula (2), it is preferable for $R_b$ that the hydroxyl group at the 5'position of the nucleoside, which provides the starting point of the nucleic acid elongation reaction, is protected with a trityl-based protecting group (for example, 4,4'-dimethoxytrityl (DMTr) group, etc.).

Similarly, when the universal linker is used, it is preferable that the hydroxyl group, which provides the starting point of the nucleic acid elongation reaction, is protected with a trityl-based protecting group (for example, 4,4'-dimethoxytrityl (DMTr) group, etc.).

The solid-phase carrier containing the linker represented by the formula (2) is typically prepared by a condensation reaction of the inorganic porous carrier containing the linker represented by the general formula (1) with the compound ($R_b$-$L_{10}$-W). This $L_{10}$ represents a linking group represented by the above-mentioned formula $L_{10}$. W represents a reactive functional group (for example, a hydroxyl group).

When the nucleoside linker is used, the nucleoside linker corresponding to the base at the 3' end is selected depending on the sequence of RNA to be synthesized. Examples of the nucleoside linker include a nucleoside linker containing a succinyl group as a functional group to be reacted with an amino group (—$NH_2$).

Examples of the nucleoside linker containing a succinyl group are shown below.

In the following formulae, each of marks * represents a bond to the imino group (—NH—) in the above-mentioned formula (2). TBDMS refers to a tert-butyldimethylsilyl group. Ac refers to an acetyl group. Me refers to a methyl group. Ph refers to a phenyl group.

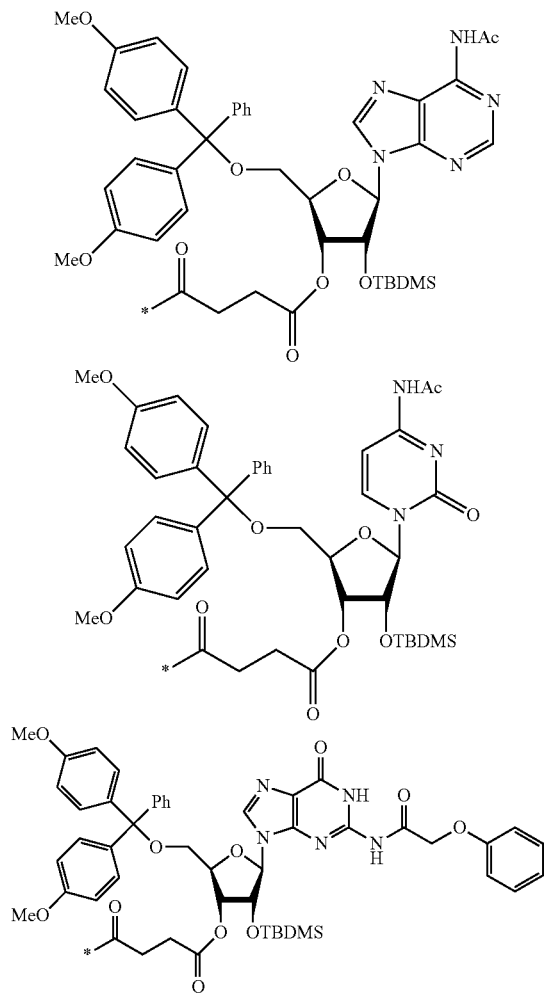

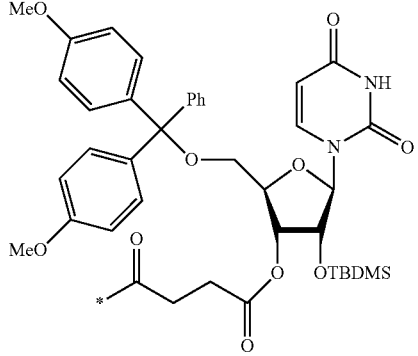

The condensation reaction as described above is carried out by mixing the inorganic porous carrier, the above-mentioned compound ($R_b$-$L_{10}$-W), the condensing agent and an appropriate solvent, and usually shaking the mixture at room temperature or heating the mixture to facilitate the condensation reaction. The condensation reaction may also be carried out by allowing the mixture to stand without shaking and with stirring.

As the condensing agent for the condensation reaction, any condensing agent to be usually used for an amide condensation can be used. Specific examples of the condensing agent include N,N'-dicyclohexylcarbodiimide (DCC), N,N'-diisopropylcarbodiimide (DIC), 1-ethyl-3-(3-dimethylaminopropyl) carbodiimide hydrochloride (EDAC), 1-ethyl-3-(3-dimethylaminopropyl)carbodiimide (EDC), 1-[bis(dimethylamino)methylene]-1H-1,2,3-triazolo[4,5-b]pyridinium 3-oxide hexafluorophosphate (HATU), 1-[bis(dimethylamino)methylene]-1H-1,2,3-benzotriazolium 3-oxide hexafluorophosphate (HBTU), 1-[bis(dimethylamino)methylene]-1H-1,2,3-triazolo[4,5-b]pyridinium 3-oxide tetrafluoroborate (TATU), 1-[bis(dimethylamino)methylene]-1H-1,2,3-benzotriazolium 3-oxide tetrafluoroborate (TBTU), (1-cyano-2-ethoxy-2-oxoethylideneaminooxy)dimethylaminomorpholinocarbenium hexafluorophosphate (COMU), O-[(ethoxycarbonyl)cyanomethyleneamino]-N, N,N',N'-tetramethyluronium hexafluorophosphate (TOTU) and the like, or a mixture of two or more thereof. Additives such as N,N-dimethyl-4-aminopyridine (DMAP) and N,N-diisopropylethylamine may be added.

The solid-phase carrier after the completion of the condensation reaction is filtered by filtration with a solvent, and collected. Examples of the solvent for filtration include acetonitrile and the like. Capping treatment to the unreacted amino group may be carried out. Examples of the capping treatment agent to be used include acetic anhydride (for example, acetic anhydride-tetrahydrofuran solution) and phenoxyacetic anhydride (for example, phenoxyacetic anhydride/N-methylimidazole solution). The success or failure of capping can be confirmed by a ninhydrin test. When a nucleoside linker or universal linker having a protecting group such as 4,4'-dimethoxytrityl (DMTr) group is used, the quantification of the reacted nucleoside can be carried out by cleaving the DMTr group with an acid and then measuring an absorbance thereof.

The amount of ($R_b$-$L_1$) supported is usually within a range of 0.1 to 5.0 μmol/m², and preferably 0.5 to 2.0 μmol/m², with respect to the specific surface area per mass of the inorganic porous substance, which is determined by $N_2$ adsorption/desorption measurement.

The solid-phase carrier of the present embodiment is preferable as a substrate for a solid-phase synthesis of nucleic acid (DNA and RNA). Further, the solid-phase carrier of the present embodiment is particularly suitable for the synthesis of RNA, which has been considered to have a problem in stability as compared with DNA.

Hereinafter, the solid-phase synthesis of RNA is illustrated as an example of the preparation method, and the method for preparing nucleic acid is described with reference to a reaction route shown below (condensation reaction, oxidation, and deprotection).

Here, with respect to the reaction route illustrated below, an example in which a nucleoside is used as $R_b$ in the formula (2) is shown.

Examples of the base represented by $R^4$ include purine bases such as adenine, isoguanine, xanthine, hypoxanthine and guanine; and pyrimidine bases such as cytosine, uracil and thymine; and the like.

Examples of the base represented by $R^4$ further include amino derivatives such as 2-aminoadenine, 2-aminopurine, and 2,6-diaminopurine; alkyl derivatives such as 5-methyluracil, 5-methylcytosine, 7-methylguanine, 6-methylpurine, 2-propylpurine; 5-halouracil and 5-halocytosine; 5-propynyluracil and 5-propynylcytosine; 6-azauracil, 6-azacytosine and 6-azathymine; 5-uracil (pseudouracil), 4-thiouracil, 5-(2-aminopropyl)uracil, and 5-aminoallyluracil; 8-substituted purines, for example, 8-halogenated, aminated, thiolated, thioalkylated or hydroxylated purine, or

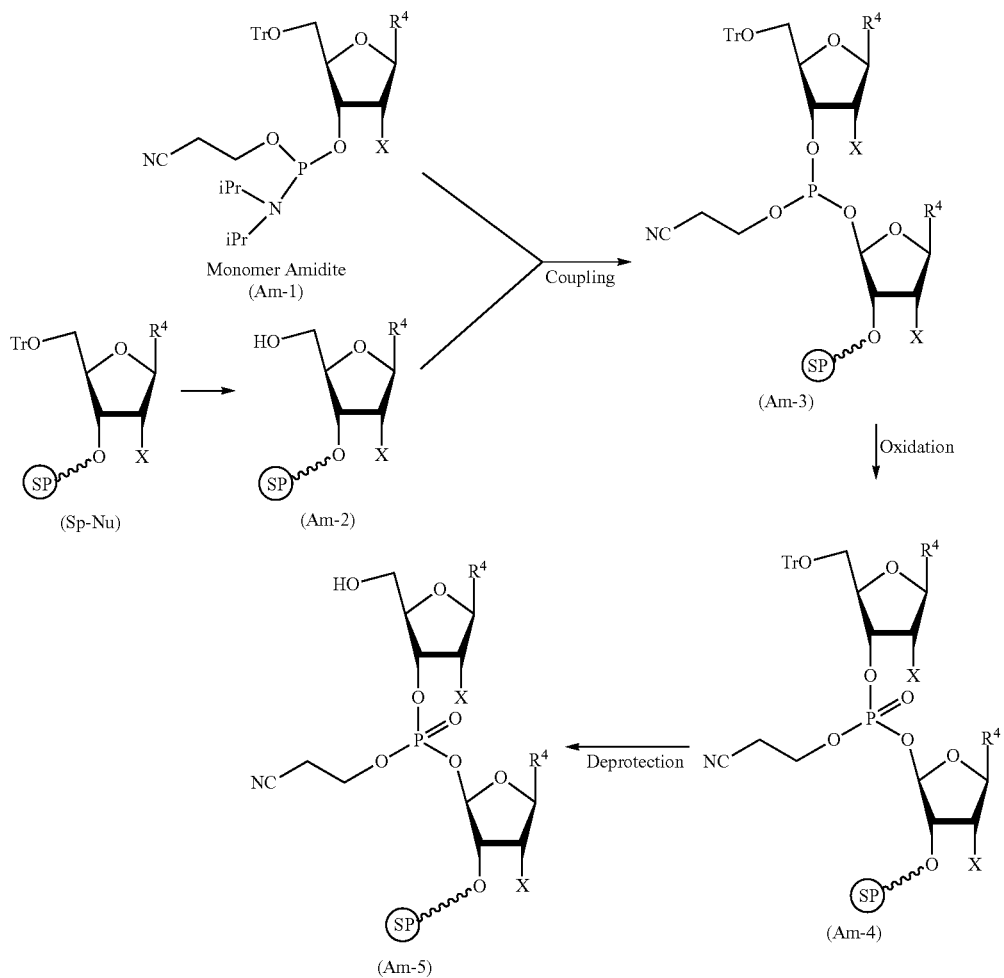

In the chemical formula shown in the above reaction route, $R^4$ represents a base; Tr represents a protecting group; and X represents —H, —OH or —OR$^5$ (wherein, R$^5$ represents a protecting group).

The base ($R^4$) constituting the nucleoside of the solid-phase carrier (Sp-Nu) containing the linker represented by the general formula (2) and the nucleoside of the amidite monomer (Am-1) is usually a nucleic acid, and typically a naturally-occurring base which is composed of RNA, however, may be a non-naturally-occurring base in some cases. Examples of such the non-naturally-occurring base include modified analogs of the naturally-occurring base or non-naturally-occurring base.

other 8-substituted purine; 5-substituted pyrimidines, for example, 5-trifluoromethylated pyrimidine, or other 5-substituted pyrimidine; 6-azapyrimidine; N-2, N-6 or O-6 substituted purines (including 2-aminopropyladenine); dihydrouracil; 3-deaza-5-azacytosine; 7-deazaadenine; N6-methyladenine, N6,N6-dimethyladenine; 5-amino-allyluracil; N3-methyluracil; substituted 1,2,4-triazole; 2-pyridinone; 5-nitroindole; 3-nitropyrrole; 5-methoxyuracil; uracil-5-oxyacetic acid; 5-methoxycarbonylmethyluracil; 2-thiouracil, 5-methyl-2-thiouracil; 5-methoxycarbonylmethyl-2-thiouracil; 5-methylaminomethyl-2-thiouracil, 3-(3-amino-3-carboxypropyl)uracil; 3-methylcytosine; N4-acetylcytosine; 2-thiocytosine; N6-methyladenine; N6-isopentyladenine; 2-methylthio-N6-isopentyladenine; N-methylguanine; O-alkylated bases, or the like; and a mixture of two or more thereof.

Further, examples of purine compounds and pyrimidine compounds include those disclosed in each of U.S. Pat. No. 3,687,808; "Concise Encyclopedia Of Polymer Science And Engineering, pp. 858-859, edited by Kroschwitz J. I., John Wiley & Sons, 1990; and Englisch et al., Angewandte Chemie, International Edition, 1991, vol. 30, p. 613.

Examples of the amidite monomer (Am-1) preferably include TBDMS amidite (TBDMS RNA Amidites, product name, ChemGenes Corporation), ACE amidite, TOM amidite, CEE amidite, CEM amidite, TEM amidite (Reviews by Chakhmakhcheva: Protective Groups in the Chemical Synthesis of Oligoribonucleotides, Russian Journal of Bioorganic Chemistry, 2013, Vol. 39, No. 1, pp. 1-21.), and EMM amidite (as described in WO2013/027843 A1), or the like, in which the protecting group $R^5$ in the compound represented by the following chemical formula (Am-1') is tert-butyldimethylsilyl (TBDMS) group, bis(2-acetoxy)methyl (ACE) group, (triisopropylsilyloxy)methyl (TOM) group, (2-cyanoethoxy)ethyl (CEE) group, (2-cyanoethoxy)methyl (CEM) group, para-tolylsulfonylethoxymethyl (TEM) group, (2-cyanoethoxy)methoxymethyl (EMM) group, or the like.

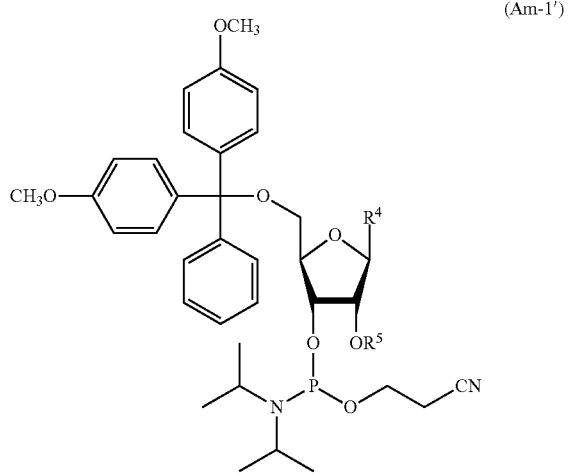

(Am-1')

[wherein, $R^5$ represents a protecting group of the hydroxyl group; and $R^4$ represents a protected nucleobase.]

The solid-phase carrier of the present embodiment may also be used to incorporate a divalent group other than a nucleoside and nucleotide into a nucleic acid sequence. For example, an amidite having a proline framework (for example, Amidite P as described later) can be incorporated into a nucleic acid sequence according to the amidite method (see the same method as the method of Example A4 of WO2012/017919 A1). Further, the amidite represented by each of the following structural formulae (Am-11), (Am-12) and (Am-13) (see Examples A1 to A3 of WO2013/103146 A1) may also be used.

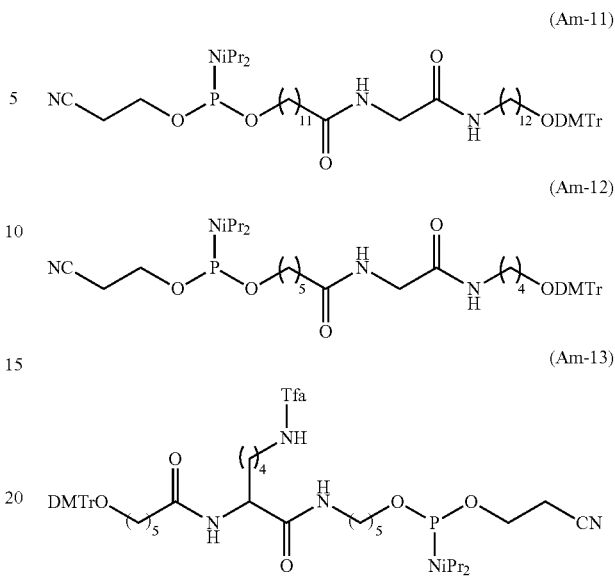

[wherein, iPr represents an isopropyl group, DMTr represents a 4,4'-dimethoxytrityl group, and Tfa represents a trifluoroacetyl group.]

[Solid-Phase Synthesis of RNA]

The solid-phase carrier (Sp-Nu) containing the linker represented by the general formula (2) is deprotected (-Tr) to obtain the solid-phase carrier (Am-2). Then, the amidite monomer (Am-1) and the solid-phase carrier (Am-2) are subjected to a condensation reaction to obtain a reaction product (Am-3). Then, the reaction product (Am-3) is oxidized to obtain the product (Am-4) Then, the product (Am-4) is deprotected (-Tr) to obtain the product (Am-5). Then, the amidite monomer (Am-1) and the product (Am-5) are further subjected to a condensation reaction to elongate the phosphodiester bond.

As described above, the hydroxyl group of the 5'position at the end of the elongated oligonucleotide strand is repeatedly subjected to a series of cycle including deprotection, condensation reaction and oxidation as many times as necessary so as to provide a desired sequence, and then the resulting product can be cleaved from the solid-phase carrier to produce a nucleic acid molecule having a desired sequence.

More specifically, a nucleic acid is prepared according to a preparation method comprising the following steps:

stop (A): a step of deprotecting the protecting group of the hydroxyl group at the 5'position of the nucleoside using the inorganic porous carrier wherein $R_b$ in the general formula (2) represents a nucleoside or nucleotide in which a hydroxyl group as a reactive group is protected;

step (B): a condensation step of subjecting the hydroxyl group at the 5'position of the nucleoside produced in the step (A) to a condensation reaction with an amidite compound having a second nucleoside base to produce a phosphite;

step (C): an oxidation step of oxidizing the phosphite produced in the step (B) to produce a nucleotide; and step (D): a step of deprotecting the protecting group of the hydroxyl group at the 5'position of the nucleotide produced in the step (C).

The preparation method comprising the above-mentioned steps (A) to (D) may optionally comprise the following steps:

step (B'): a step of further subjecting the product produced in the step (D) to a condensation reaction with an amidite compound having a nucleoside base to be introduced in next time to produce a phosphite;

step (C'): a step of oxidizing the phosphite produced in the step (B') to produce an oligonucleotide;

step (D'): a step of deprotecting the protecting group of the hydroxyl group at the 5'position in the end of the oligonucleotide strand produced in the step (C'); and step (E): a step of carrying out a series of steps consisting of the above step (B'), step (C') and step (D') repeatedly m times (wherein m is an integer of 1 or more) to react the number of m of amidite compounds (nucleic acid elongation reaction), and then cleaving an elongated nucleic acid.

The nucleic acid elongation reaction of the present embodiment can be carried out according to the procedure of a general phosphoramidite method.

The "nucleic acid elongation reaction" herein refers to a reaction in which a nucleic acid strand, particularly RNA strand, is elongated by sequentially binding nucleotides through a phosphodiester bond. The nucleic acid elongation reaction may be carried out by means of an automatic nucleic acid synthesizer or the like that employs the phosphoramidite method.

In the deprotection step, the protecting group of the hydroxyl group at the 5'position in the end of the RNA strand supported on the solid-phase carrier is deprotected. As a general protecting group, a trityl-based protecting group (typically, a DMTr group) is used. The deprotection can be carried out with an acid. Examples of the acid for deprotection include trifluoroacetic acid, trichloroacetic acid, dichloroacetic acid, trifluoromethanesulfonic acid, methanesulfonic acid, hydrochloric acid, acetic acid, p-toluenesulfonic acid, and the like, or a mixture of two or more thereof.

In the condensation step, the nucleoside phosphoramidite is bound to the hydroxyl group at the 5'position in the end of the RNA strand which is deprotected by the above-mentioned deprotection step so as to produce the phosphite. As the nucleoside phosphoramidite, a nucleoside phosphoramidite in which the hydroxyl group at the 5'position is protected with a protecting group (for example, DMTr group) is used.

Further, the condensation step can be carried out with an activator which activates the nucleoside phosphoramidite. Examples of the activator include 5-benzylthio-1H-tetrazole (BTT), 1H-tetrazole, 4,5-dicyanoimidazole (DCI), 5-ethyl-thio-1H-tetrazole (ETT), N-methylbenzimidazolium triflate (N-MeBIT), benzimidazolium triflate (BIT), N-phenylimidazolium triflate (N-PhIMT), imidazolium triflate (IMT), 5-nitrobenzimidazolium triflate (NBT), 1-hydroxybenzotriazole (HOBT), 5-(bis-3,5-trifluoromethylphenyl)-1H-tetrazole (Activator-42), and the like, or a mixture of two or more thereof.

After the condensation step, an unreacted hydroxyl group at the 5'position may be capped as needed. The capping can be carried out with a publicly known capping solution such as acetic anhydride-tetrahydrofuran solution, phenoxyacetic acid/N-methylimidazole solution, and the like, or a mixture of two or more thereof.

The oxidation step refers to a step of oxidizing the phosphite formed by the condensation step. The oxidation step can be carried out with an oxidizing agent. Examples of the oxidizing agent include iodine, m-chloroperbenzoic acid, tert-butylhydroperoxide, 2-butanoneperoxide, bis(trimethylsilyl)peroxide, 1,1-dihydroperoxycyclododecane, hydrogen peroxide, and the like, or a mixture of two or more thereof.

The oxidation step may be carried out after the capping operation as described above, or conversely, the capping operation may be carried out after the oxidation step, and accordingly an order of them is not limited thereto.

After the oxidation step, the process returns to the deprotection step, and the above-mentioned steps including condensation reaction, oxidation and deprotection can be repeated depending on a nucleotide sequence of RNA to be synthesized so as to synthesize RNA having a desired sequence.

After the synthesis of the RNA strand having the desired sequence is completed, the RNA strand is cleaved from the solid-phase carrier by ammonia, amines, or the like, and collected.

Examples of the amines as describe above include methylamine, ethylamine, isopropylamine, ethylenediamine, diethylamine, triethylamine, and the like, or a mixture of two or more thereof.

When the universal linker is used, after the completion of the synthesis of RNA strand, the RNA strand is cleaved from the solid-phase carrier by ammonia, amines, or the like, and the universal linker is eliminated with a nucleophile. Once the elimination is completed, the 3' position of a terminal nucleotide is changed to a hydroxyl group, and the phosphate is bound to the universal linker to form a cyclic phosphodiester. The collected RNA may be purified by a publicly known method, as needed.

In the present embodiment as described above, the inorganic porous substance is modified with the aminosilane containing substituents ($R^1$, $R^2$). In the inorganic porous carrier of the present embodiment, the above substituents ($R^1$, $R^2$) can inhibit the overcrowded modification of aminosilane to the carrier such that the amino groups is introduced into the carrier in a state where the amino groups are appropriately away from each other. When the amino groups are away from each other in such a manner, steric hindrance between oligonucleic acids is unlikely to occur during the nucleic acid elongation reaction, and the elongation reaction can easily proceed stably to achieve the target strand length. Accordingly, when the inorganic porous carrier of the present embodiment is used, the yield can be further improved in the preparation of RNA. Further, according to the method for preparing RNA of the present embodiment, the yield can be further improved in the preparation of RNA, and particularly a long-stranded RNA can be obtained more stably in higher yield.

In addition, when the inorganic porous carrier of the present embodiment is applied to the nucleic acid synthesis, highly pure RNA can be obtained in high yield, even if long-stranded RNA of 40-mer or more is synthesized.

The "yield of RNA" herein refers to a percentage (%) of an actually isolated RNA to an amount of RNA theoretically calculated based on an amount of nucleoside provided for the reaction. The amount of nucleic acid is calculated from the measurement of UV absorbance. Specifically, in the method for the above measurement, the nucleic acid is dissolved in water or a buffered aqueous solution, and placed in a cell having an optical path length of 1 cm. The optical concentration C is calculated from the absorbance at a wavelength of 260 nm measured by a UV absorptiometer according to the following equation to determine the amount of nucleic acid. The coefficient to be used is 40 μg/mL.

$$C = a \times L \times A_{260}$$

($A_{260}$: absorbance, a: coefficient, L: optical path length, C: optical concentration)

The "purity of RNA" refers to a percentage (%) at which the nucleic acid having the target strand length is obtained. It is determined based on an area percentage (that is, a percentage of measured area) or a 10% width of a main peak in a chromatogram obtained by liquid chromatography.

EXAMPLES

Hereinafter, the present invention is described in more detail with reference to Examples, however, the present invention should not be limited to these examples.

<Preparation of Inorganic Porous Substance>

Each of SP (1) to SP (7) as described below was used as the inorganic porous substance. In each of the inorganic porous substances SP (1) to SP (7), the pore size (mode diameter; μm), the particle size (median diameter; μm), the surface area per volume of the inorganic porous substance ($m^2$/mL), and the porosity (%) were determined. The results are shown in Tables 1 and 2.

The pore size (mode diameter; μm) and the porosity (%) were determined by the mercury intrusion method. The particle size (μm) was determined based on the median diameter measured by laser diffraction (scattering type). The surface area per volume ($m^2$/mL) was determined by multiplying the bulk density (g/mL), which was measured by the mercury intrusion method, by the specific surface area per mass the inorganic porous substance ($m^2$/g), which was measured by $N_2$ adsorption/desorption isotherm measurement.

Inorganic Porous Substance SP (1):

A molded zeolite substance was obtained in the same manner as in Example 1 described in JP 5875843 B2. The resulting molded zeolite substance was suspended in a solvent of acetonitrile to prepare a suspension. Then, the suspension was sieved with a JIS sieve having an opening size of 125 μm and successively with a JIS sieve having an opening size of 38 μm. Then, the powdery solid remaining on the sieve having an opening size of 38 μm was dried by air at room temperature to prepare the inorganic porous substance SP (1) as a white powdery solid.

Inorganic Porous Substance SP (2):

As the inorganic porous substance SP (2), a commercially available spherical silica gel powder (trade name: M.S.GEL, produced by AGC Si-Tech Co., Ltd.) was used.

Inorganic Porous Substance SP (3):

A calcined zeolite substance was obtained in the same manner as in Example 1 described in JP 5875843 B2. Then, 10 g of the resulting calcined substance was put in a petri dish, and stood in a two-liter separable flask containing 100 mL of water, and the separable flask was closed with a lid. Then, the separable flask was placed in a constant temperature water bath at 80° C., and left to stand for 24 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly nine times, and then washed with water, and dried to obtain the inorganic porous substance SP (3).

Inorganic Porous Substance SP (4):

In a stainless steel autoclave with a capacity of 1.5 L, tetraethyl orthosilicate [$Si(OC_2H_5)_4$] 115 g, 40% by mass tetra-n-propylammonium hydroxide aqueous solution 57 g, potassium hydroxide (purity 85%) 0.9 g and water 325 g were placed, and the mixture was vigorously stirred at room temperature for 120 minutes. The molar ratios of water, tetra-n-propylammonium ion, hydroxide ion and potassium ion to silicon in the obtained mixed solution were 36, 0.20, 0.24 and 0.048, respectively. The mixed solution was stirred at 105° C. for 48 hours at a rotation speed of 300 rpm, and subjected to a hydrothermal synthesis reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530° C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 34 hours. The separable flask was taken out, and allowed to cool to 20° C. The resulting solid 4 g was placed in an autoclave, and a mixed solution 278 g of 7.5% by mass ammonium nitrate aqueous solution 110 g and 25% by mass ammonia aqueous solution 168 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly three times, and then washed with water, and dried. Finally, the obtained white solid was pulverized in a mortar, and sieved with sieves having an opening size of 106 μm and successively an opening size of 38 μm to obtain the inorganic porous substance SP (4).

Inorganic Porous Substance SP (5):

In a stainless steel autoclave with a capacity of 1.5 L, tetraethyl orthosilicate [$Si(OC_2H_5)_4$] 155 g, 40% by mass tetra-n-propylammonium hydroxide aqueous solution 136 g, potassium hydroxide (purity 85%) 0.3 g and water 162 g were placed, and the mixture was vigorously stirred at room temperature for 120 minutes. The molar ratios of water, tetra-n-propylammonium ion, hydroxide ion and potassium ion to silicon in the obtained mixed solution were 18, 0.36, 0.38 and 0.048, respectively. The mixed solution was stirred at 105° C. for 48 hours at a rotation speed of 300 rpm, and subjected to a hydrothermal synthesis reaction. The resulting reaction mixture was filtered, and washed repeatedly with pure water until the pH of the filtrate was made 9.0 or less. The obtained wet cake was dried at 110° C., and then pulverized in a mortar. The obtained pulverized substance was sieved with a sieve having an opening size of 2.36 mm and successively a sieve having an opening size of 1.00 mm. The obtained substance was calcined in a tubular furnace at 530° C. for 1 hour under nitrogen flow, and then further calcined at 530° C. for 1 hour under flow of a mixed gas of nitrogen and air [nitrogen: air (volume ratio)=9:1] to obtain a white calcined substance.

Next, 10 g of the calcined substance as obtained above was put in a petri dish, and stood in a two-liter separable flask containing 100 mL of water, and the separable flask was closed with a lid. Then, the separable flask was placed in a constant temperature water bath at 80° C. for 5 hours. The separable flask was taken out, and allowed to cool to 20° C. The resulting solid 8 g was placed in an autoclave, and a mixed solution 222 g of 7.5% by mass ammonium nitrate aqueous solution 88 g and 25% by mass ammonia aqueous solution 134 g was added thereto, and the mixture was stirred at 90° C. for 1 hour, and then the solid was separated by filtration. The solid was further treated with the mixed solution of the ammonium nitrate aqueous solution and the ammonia aqueous solution prepared in the same manner as described above repeatedly twice, and then washed with water, and dried. Finally, the obtained white solid was pulverized in a mortar, and sieved with sieves having an opening size of 106 μm and successively an opening size of 38 μm to obtain the inorganic porous substance SP (5).

Inorganic Porous Substance SP (6):

In a stainless steel autoclave with a capacity of 1600 L, tetraethyl orthosilicate [$Si(OC_2H_5)_4$] 186 kg, 40% by mass tetra-n-propylammonium hydroxide aqueous solution 166 kg, potassium hydroxide (purity 85%) 0.3 kg and water 490 kg were placed, and the mixture was stirred at room temperature for 120 minutes. The molar ratios of water, tetra-n-propylammonium ion, hydroxide ion and potassium ion to silicon in the obtained mixed solution were 37, 0.36, 0.39 and 0.049, respectively. The mixed solution was stirred at 105° C. for 12 hours at a rotation speed of 60 rpm, and subjected to a hydrothermal synthesis reaction. The resulting reaction mixture was washed with pure water in the same manner as in the inorganic porous substance SP (5). After washing, the slurry containing crystals was collected. The slurry was spray-dried with an atomizer-type spray dryer, and formed into particles. The particles were calcined at 550° C. for 2.5 hours under nitrogen flow, and then calcined at 550° C. for 2.5 hours under flow of a mixed gas of nitrogen and air [nitrogen:air (volume ratio)=3:1] to obtain a white calcined substance.

Next, 50 g of the calcined substance as obtained above was put in a petri dish, and stood in a separable flask containing 100 mL of water, and the separable flask was closed with a lid. Then, the separable flask was placed in a constant temperature water bath at 80° C. for 4 hours. The resulting solid 5.00 g was placed in an autoclave, a mixed solution 444 g of 7.5% by mass ammonium nitrate aqueous solution 176 g and 25% by mass ammonia aqueous solution 268 g was added thereto, and the mixture was stirred at 86° C. for 1 hour, and then the solid was separated by filtration. The solid was further treated with the mixed solution of the ammonium nitrate aqueous solution and the ammonia aqueous solution prepared in the same manner as described above repeatedly four times, and then washed with water, and dried to obtain the inorganic porous substance SP (6).

Inorganic Porous Substance SP (7):

As the inorganic porous substance SP (7), a commercially available porous glass (trade name: CPG-1000, produced by Geneact Co., Ltd.) was used.

<Synthesis of Silane Coupling Agent>

As the silane coupling agent, ingredient (C1), ingredient (C2), ingredient (C3), ingredient (C4), ingredient (C5), ingredient (C6), and ingredient (C7) as described below were used.

Ingredient (C1):

3-Aminopropyldiisopropylethoxysilane which was commercially available was purchased and used.

Ingredient (C2):

Trichlorosilane (5 mL, 50 mmol), 6-chloro-1-hexene (3.80 g, 32 mmol) and a solution of hydrogen hexachloroplatinate (IV) hexahydrate (1 M, 5 μL, 5 μmol) in isopropanol was stirred at room temperature for 18.5 hours. THF (50 mL) was added to the resulting mixed solution, a solution of isopropyl magnesium chloride (1 M, 150 mL, 150 mmol) in THF was slowly added dropwise under ice-cooling, and the mixture was stirred at room temperature for 73.5 hours. The resulting reaction solution was added dropwise to a mixed solution of isopropanol (40 mL), triethylamine (80 mL) and THF (120 mL) under ice-cooling, and the mixture was stirred at room temperature for 1.5 hours, and then the insoluble material was removed by filtration. The solvent was evaporated under reduced pressure, and hexane (30 mL) was added to the resulting residue, and the insoluble material was removed by filtration, and then the filtrate was concentrated under reduced pressure to obtain 4.37 g of 6-chlorohexylisopropoxydiisopropylsilane (yield 47%).

A solution of ammonia (7N, 21.4 mL, 150 mmol) in methanol was added to the obtained 6-chlorohexylisopropoxydiisopropylsilane (1.46 g, 5 mmol) in a sealed-type melting crucible, and the mixture was stirred at 142° C. for 3 hours. The resulting mixture was poured into THF (200 mL), and the mixture was filtered, and then the solvent of the filtrate was evaporated under reduced pressure. Heptane (20 mL) was added to the resulting residue, the insoluble material was removed by filtration, and the solvent was evaporated under reduced pressure to obtain 1.83 g of 6-aminohexylisopropoxydiisopropylsilane.

The obtained compound was subjected to NMR measurement, and a structure thereof was identified from the following measurement results.

$^1$H-NMR (400 MHz, CDCl3) δ: 10.90-1.11 (18H, m), 1.13-1.45 (10 h, m), 2.92-2.96 (2H, m), 4.00-4.04 (1H, m)

Ingredient (C3):

3-Chloropropyltrimethoxysilane (3.97 g, 20 mmol) was added to tetrahydrofuran (THF) (20 mL), the mixture was cooled to 5° C., and a solution of phenylmagnesium bromide (1 M, 60 mL, 60 mmol) in THF was slowly added dropwise.

Then, the mixture was stirred at room temperature for 15 and a half hours. Ethanol 4.36 mL was added to the reaction solution, and the mixture was stirred at room temperature for 1 hour. The solvent was evaporated under reduced pressure, and the resulting residue was subjected to silica gel column chromatography (eluent: hexane) to obtain 3.61 g of 3-chloropropyldiphenylmethoxysilane (yield 62%).

Methanol (2 mL) and ammonia methanol solution (7N, 10 mL, 72 mmcl) were added to the obtained 3-chloropropyldiphenylmethoxysilane (0.7 g, 2.4 mmol) in a sealed-type melting crucible, and the mixture was stirred at 142° C. for 3 hours.

The resulting mixture was poured into THF (100 mL), and the mixture was filtered, and then the solvent of the filtrate was evaporated under reduced pressure. Heptane (10 mL) and methanol (10 mL) were added to the resulting residue, and the solvent in the methanol layer was evaporated under reduced pressure to obtain 0.4 g of 3-aminopropyldiphenylmethoxysilane (yield 61%).

The obtained compound was subjected to NMR measurement, and a structure thereof was identified from the following measurement results.

$^1$H-NMR (400 MHz, CDCl$_3$) δ: 1.20 (2H, dd), 1.78 (2H, m), 2.94 (2H, m), 3.44 (3H, s), 7.24-7.58 (10H, m)

Ingredient (C4):

Trichlorosilane (2 mL, 20 mmol) was added to n-hexane (20 mL), and the mixture was stirred, and then a solution of n-butyllithium (1.6 M, 27.5 mL, 44 mmol) in hexane was slowly added dropwise, and the mixture was stirred at room temperature for 1.5 hours. Ethanol (5 mL) and triethylamine (5 mL) were added thereto, and the insoluble material was removed by filtration, and the solvent was evaporated under reduced pressure. The resulting residue was subjected to distillation (~70° C., 7 mmHg) with Kugelrohr apparatus to obtain 0.53 g of dibutylethoxysilane (yield 54%).

The obtained dibutylethoxysilane (0.49 g, 2.6 mmol), allylamine (0.15 g, 2.6 mmol) and a solution of hydrogen hexachloroplatinate (IV) hexahydrate (1 M, 1.3 μL, 1.3 μmol) in isopropanol were stirred at 100° C. for 1 hour. Allylamine (0.15 g, 2.6 mmol) and a solution of hydrogen hexachloroplatinate (IV) hexahydrate (1 M, 5 μL, 5 μmol) in isopropanol were added thereto, and the mixture was further stirred for 2 hours. The resulting mixture was subjected to distillation (~120° C., 5 mmHg) with Kugelrohr apparatus to obtain 0.26 g of 3-aminopropyldibutylethoxysilane (yield 41%).

Ingredient (C5):

3-Aminopropyldimethylethoxysilane (Aldrich, CAS RN: 18306-79-1 product code: 588857) was used.

Ingredient (C6):

3-Aminopropyltriethoxysilane (TCT, CAS RN: 919-30-2, product code: A0439) was used.

Ingredient (C7):

A solution of hydrogen hexachloroplatinate (IV) hexahydrate (1 M, 9.7 μL, 9.7 μmol) in isopropanol was added to a solution of chlorodiisopropylsilane (5.0 mL, 37.5 mmol) and allylbromide (1.6 mL, 18.8 mmol) in toluene (26 mL), and the mixture was stirred at 140° C. for 3 hours. The reaction mixture was cooled, ethanol and triethylamine were poured thereinto, and the mixture was further stirred. The resulting precipitate was filtered, and the filtrate was concentrated to obtain a mixture containing 3-bromopropyldiisopropylethoxysilane. Then, 1,6-diaminohexane (0.58 g, 5.0 mmol) was added thereto, and the reaction was carried out at 100° C. for 2 hours. The resulting mixture was filtered, and evaporated under reduced pressure, and then subjected to silica gel column purification (chloroform/ethanol=80/20) to obtain [3-(6-aminohexylamino)propyl]diisopropylethoxysilane (0.36 g, 22%).

<Method for Preparing Inorganic Porous Substance Supporting Linker (Inorganic Porous Carrier)>

The inorganic porous carrier of each of examples was obtained by treating the surface of any one of the inorganic porous carriers SP (1) to SP (7) with any one of the ingredients (C1) to (C7) as the silane coupling agents.

Example 1

The inorganic porous substance SP (1) 2.00 g was placed in a four-necked flask, and toluene 100 mL was added thereto. The ingredient (C1) 4.8 mg was further added thereto under stirring, and the mixture was stirred at room temperature for 3 hours. Then, the reaction solution was filtered, and washed with toluene, and then the residue was dried under reduced pressure to obtain the inorganic porous carrier of Example 1.

Example 2

The inorganic porous carrier of Example 2 was obtained in the same manner as the preparation method of Example 1 except for that the ingredient (C1) was replaced with the ingredient (C2) (addition amount: 27.2 mg).

Example 3

The inorganic porous carrier of Example 3 was obtained in the same manner as the preparation method of Example 1 except for that the ingredient (C1) was replaced with the ingredient (C3) (addition amount: 14.2 mg).

Example 4

The inorganic porous carrier of Example 4 was obtained in the same manner as the preparation method of Example 1 except for that the ingredient (C1) was replaced with the ingredient (C4) (addition amount: 8.3 mg).

Example 5

The inorganic porous carrier of Example 5 was obtained in the same manner as the preparation method of Example 1 except for that the inorganic porous substance SP (1) was replaced with the inorganic porous substance SP (2) (1.00 g) and the addition amount of the ingredient (C1) was changed to 2.4 mg.

Example 6

The inorganic porous carrier of Example 6 was obtained in the same manner as the preparation method of Example 1 except for that the inorganic porous substance SP (1) was replaced with the inorganic porous substance SP (3) (2.00 g) and the addition amount of the ingredient (C1) was changed to 6.8 mg.

Example 7

The inorganic porous carrier of Example 7 was obtained in the same manner as the preparation method of Example 1 except for that the inorganic porous substance SP (1) was replaced with the inorganic porous substance SP (4) (0.40 g) and the addition amount of the ingredient (C1) was changed to 1.2 mg.

Example 8

The inorganic porous carrier of Example 8 was obtained in the same manner as the preparation method of Example 1 except for that the inorganic porous substance SP (1) was replaced with the inorganic porous substance SP (5) (2.00 g) and the addition amount of the ingredient (C1) was changed to 9.5 mg.

Example 9

The inorganic porous carrier of Example 9 was obtained in the same manner as the preparation method of Example 1 except for that the inorganic porous substance SP (1) was replaced with the inorganic porous substance SP (6) (0.35 g) and the addition amount of the ingredient (C1) was changed to 3.0 mg.

Example 10

The inorganic porous carrier of Example 10 was obtained in the same manner as the preparation method of Example 1 except for that the silane coupling agent which was added to the inorganic porous substance SP (1) (1.00 g) was changed from the ingredient (C1) to the ingredient (C7) (addition amount: 7.1 mg).

Example 11

Ingredient (C1) (55 mg) and toluene (72.32 g) were mixed in a glass vial to prepare a solution of ingredient (C1)/toluene. The inorganic porous substance SP (7) (7.00 g) was placed in a round-bottom flask, and the prepared solution of ingredient (C1)/toluene (34.23 g) was added thereto at room temperature. The round-bottom flask was introduced into an nil bath at 100° C., and the mixture was reacted for 5 hours. Then, the reaction mixture was filtered, and the solid content was washed with toluene, and then dried under reduced pressure to obtain the inorganic porous carrier of Example 11.

Comparative Example 1

The inorganic porous carrier of Comparative Example 1 was obtained in the same manner as the preparation method of Example 1 except for that the ingredient (C1) was replaced with the ingredient (C5) (addition amount: 3.8 mg).

Comparative Example 2

The inorganic porous carrier of Comparative Example 2 was obtained in the same manner as the preparation method of Example 1 except for that the ingredient (C1) was replaced with the ingredient (C6) (addition amount: 4.9 mg).

Comparative Example 3

The inorganic porous carrier of Comparative Example 3 was obtained in the same manner as the preparation method of Example 1 except for that the inorganic porous substance SP (1) was replaced with the inorganic porous substance SP (2) (1.00 g) and the ingredient (C1) was replaced with the ingredient (C6) (addition amount: 2.4 mg).

Comparative Example 4

The inorganic porous carrier of Comparative Example 4 was obtained in the same manner as the preparation method of Example 1 except for that the inorganic porous substance SP (1) was replaced with the inorganic porous substance SP (3) (0.50 g) and the ingredient (C1) was replaced with the ingredient (C6) (addition amount: 2.7 mg).

Comparative Example 5

Ingredient (C6) (54 mg) and toluene (72.32 g) were mixed in a glass vial to prepare a solution of ingredient (C6)/toluene. The inorganic porous substance SP (7) (7.00 g) was placed in a round-bottom flask, and the prepared solution of ingredient (C6)/toluene (34.23 g) was added thereto at room temperature. The round-bottom flask was introduced into an oil bath at 100° C., and the mixture was reacted for 5 hours. Then, the reaction mixture was filtered, and the solid content was washed with toluene, and then dried under reduced pressure to obtain the inorganic porous carrier of Comparative Example 5.

<Preparation of Solid-Phase Carrier>

Examples 1 to 10 and Comparative Examples 1 to 4

U-succinate (5'-O-dimethoxytrityl-2'-O-tert-butyldimethylsilyl-3'-O-succinyluridine) 25.1 mg, 1-[bis(dimethylamino)methylene]-1H-1,2,3-benzotriazolium 3-oxide hexafluorophosphate (HBTU) 12.5 mg, N,N-diisopropylethylamine 5.9 µL and acetonitrile 2.7 mL were mixed, and the inorganic porous carrier 300.0 mg of each of Examples 1 to 10 and Comparative Examples 1 to 4 was added to the mixture.

The mixture was left to stand at 25° C. for 18 hours, and then filtered, and the solid (residue) was washed with acetonitrile 10 mL. A solution 1 mL of acetic anhydride and 2,6-lutidine in THF (volume ratio of acetic anhydride/2,6-lutidine/THF: 1/1/8) and a solution 1 mL of N-methylimidazole in THF (volume ratio of N-methylimidazole/THF: 16/84) were added to the washed solid. The mixture was left to stand for 1 minute, and then filtered, and the solid was washed with acetonitrile 10 mL. The washed solid was dried under vacuum to obtain the solid-phase carrier in which the nucleoside was supported on the inorganic porous carrier.

Example 11 and Comparative Example 5

U-succinate (5'-O-dimethoxytrityl-2'-O-tert-butyldimethylsilyl-3'-O-succinyluridine) 211 mg, 1-[bis(dimethylamino)methylene]-1H-1,2,3-benzotriazolium 3-oxide hexafluorophosphate (HBTU) 105 mg, N,N-diisopropylethylamine 121 µL and acetonitrile 11 mL were mixed in a glass vial. The prepared mixed solution 1.63 mL was mixed with the inorganic porous carrier 300.0 mg of each of Example 11 and Comparative Example 5. The mixture was left to stand at 25° C. for 18 hours, and then filtered, and the solid (residue) was washed with acetonitrile 10 mL. A solution 1 mL of acetic anhydride and 2,6-lutidine in THE (volume ratio of acetic anhydride/2,6-lutidine/THF: 1/1/8) and a solution 1 mL of N-methylimidazole in THF (volume ratio of N-methylimidazole/THF: 16/84) were added to the washed solid. The mixture was left to stand for 1 minute, and then filtered, and the solid content was washed with acetonitrile 10 mL. The washed solid content was dried under vacuum to obtain the solid-phase carrier in which the nucleoside was supported on the inorganic porous carrier.

(Measurement of Density of Grafted Nucleoside)

An aqueous 70% perchloric acid solution was diluted with methanol to prepare a solution of 30% perchloric acid/methanol. The solid-phase carrier 10 mg of each of Examples 1 to 11 and Comparative Examples 1 to 5 as prepared above, which supported the nucleoside, was placed in a measuring flask, and was diluted to 10 mL with the solution of 30% perchloric acid/methanol. The resulting solution was further diluted 10-fold with the solution of 30% perchloric acid/methanol, and then an absorbance thereof at 498 nm was measured, and the density of grafted nucleoside was calculated based on the following formula. The results are shown in Tables 1 and 2.

$$\text{Density of Grafted Nuceloside } [\mu\text{mol}/\text{m}^2] = \frac{(14.3 \times (\text{Absorbance at 498 nm}) \times 10 \times 10)}{(\text{Mass of Solid}-\text{phase Carrier (mg)}) \times (\text{Specific Surface Area of Inorganic Porous Carrier (m}^2/\text{g})) \div 1000)}$$

<Solid-Phase Synthesis of Oligonucleic Acid>

```
Sequence (A):
                                    (SEQ ID NO: 1, 2)
5'-GCAGAGUACACACAGCAUAUACC-P-
GGUAUAUGCUGUGUGUACUCUGCUU-3' (49-mer).

(SEQ ID NO: 1)
GCAGAGUACACACAGCAUAUACC
and (SEQ ID NO: 2)
GGUAUAUGCUGUGUGUACUCUGCUU.

Sequence (B):
                                    (SEQ ID NO: 3)
5'-AUAACUCAAUUUGUAAAAAAGUUUUAGAGCUAGAAAUAGCAAGUUA
AAAUAAGGCUAGUCCGUUAUCAACUUGAAAAAGUGGCACCGAGUCGGUG
CUUUUUUU-3' (103-mer).
```

In the above sequence (A), P represents a binding moiety separated with wavy lines in the following structure.

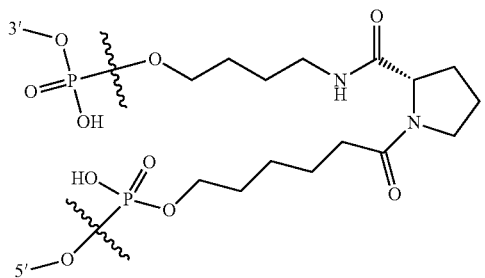

The oligonucleotide consisting of the sequence (A) or the sequence (B) was synthesized from the 3'side to the 5'side according to the phosphoramidite method by means of a nucleic acid synthesizer (trade name: NTS M-4-MX-E, produced by Nihon Techno Service Co., Ltd.) (see the reaction route (condensation reaction, oxidation, and deprotection as described above)).

Each of solid-phase carriers as prepared above was used for the above solid-phase synthesis.

As the amidite monomer, the adenosine EMM amidite (described in Example 4 of US2012/035246 A1), the cytidine EMM amidite (described in Example 3 of the same US patent literature), the guanosine EMM amidite (described in Example 5 of the same US patent literature), the uridine EMM amidite (described in Example 2 of the same US patent literature) and amidite P (described in WO2017/188042 A1) as shown below were used.

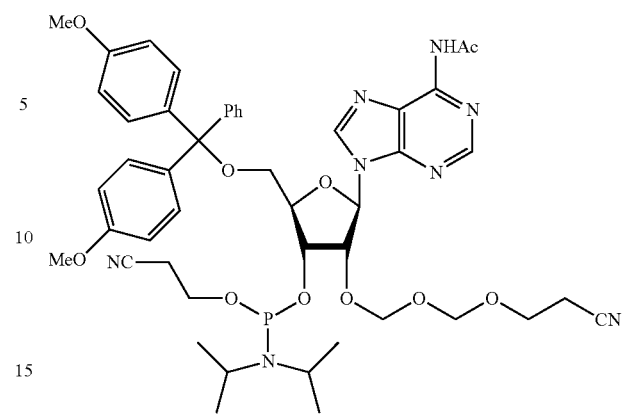

Adenosine EMM Amidite

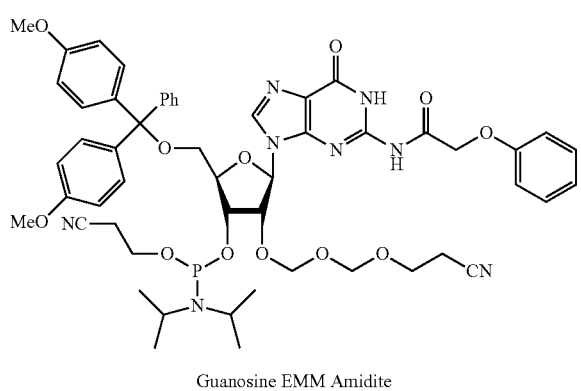

Cytidine EMM Amidite

Guanosine EMM Amidite

-continued

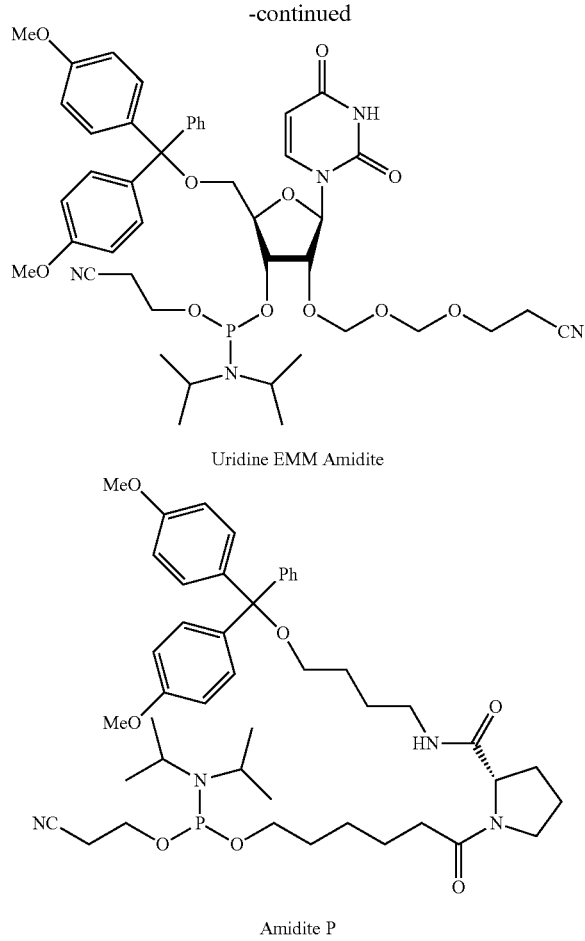

Uridine EMM Amidite

Amidite P

Further, in the solid-phase synthesis, a solution of high-purity trichloroacetic acid in toluene was used as a deblocking solution, 5-benzylmercapto-1H-tetrazole was used as a condensing agent, an iodine solution was used as an oxidizing agent, and a phenoxyacetic acid solution and an N-methylimidazole solution were used as a capping solution.

The solid-phase carrier after the completion of synthesis was placed in a glass vial with a lid, and a solution of 28% $NH_4OH$ and EtOH at a ratio of 1:1 to 2:1 was added thereto. Then, the mixture was left to stand at 40° C. for 4 hours. The solution after the completion of reaction was filtered, and washed with water and EtOH successively. The resulting solution was dried to obtain a crude oligonucleotide having a protected group. Then, the crude oligonucleotide was deprotected by the treatment with tetra-n-butylammonium fluoride (TBAF) in the presence of nitromethane to obtain the crude product.

[Measurement of Oligonucleic Acid Yield]

The absorbance $OD_{260}$ of the solution prepared from the resulting crude oligonucleotide at a wavelength of 260 nm was measured by a UV absorptiometer, and the amount of product was calculated, and the yield (%) of oligonucleic acid synthesis according to each of the solid-phase carriers were determined. The results are shown in Table 1.

TABLE 1

| | Inorganic Porous Carrier represented by General Formula (1) | | | | Pore Size | Particle Size | Pore Volume |
|---|---|---|---|---|---|---|---|
| | Inorganic Porous Substance | Substance | $R^1, R^2$ | L | mode diameter (μm) | median diameter (μm) | per Volume (mL/mL) |
| Example 1 | SP (1) | Zeolite | Isopropyl Group | $CH_2$ | 0.081 | 48 | 0.29 |
| Example 2 | SP (1) | Zeolite | Isopropyl Group | $(CH_2)_4$ | 0.081 | 48 | 0.29 |
| Example 3 | SP (1) | Zeolite | Phenyl Group | $CH_2$ | 0.081 | 48 | 0.29 |
| Example 4 | SP (1) | Zeolite | n-Butyl Group | $CH_2$ | 0.081 | 48 | 0.29 |
| Example 5 | SP (2) | Silica Gel | Isopropyl Group | $CH_2$ | 0.11 | 40 | 0.38 |
| Example 6 | SP (3) | Zeolite | Isopropyl Group | $CH_2$ | 0.11 | 48 | 0.34 |
| Example 7 | SP (4) | Zeolite | Isopropyl Group | $CH_2$ | 0.16 | 68 | 0.27 |
| Example 8 | SP (5) | Zeolite | Isopropyl Group | $CH_2$ | 0.052 | 85 | 0.24 |
| Example 9 | SP (6) | Zeolite | Isopropyl Group | $CH_2$ | 0.08 | 62 | 0.42 |
| Example 10 | SP (1) | Zeolite | Isopropyl Group | $(CH_2)_2$ $NH (CH_2)_5$ | 0.081 | 48 | 0.29 |
| Example 11 | SP (7) | Glass | Isopropyl Group | $CH_2$ | 0.11 | 210 | 0.29 |

TABLE 1-continued

| | | | | | | | |
|---|---|---|---|---|---|---|---|
| Comparative Example 1 | SP (1) | Zeolite | Methyl Group | CH$_2$ | 0.081 | 48 | 0.29 |
| Comparative Example 2 | SP (1) | Zeolite | Ethoxy Group | CH$_2$ | 0.081 | 48 | 0.29 |
| Comparative Example 3 | SP (2) | Silica Gel | Ethoxy Group | CH$_2$ | 0.11 | 40 | 0.38 |
| Comparative Example 4 | SP (3) | Zeolite | Ethoxy Group | CH$_2$ | 0.11 | 48 | 0.34 |
| Comparative Example 5 | SP (7) | Glass | Ethoxy Group | CH$_2$ | 0.11 | 209 | 0.29 |

| | Surface Area per Volume (m$^2$/mL) | Porosity (%) | Density Of Grafted Nucleoside (μmol/m$^2$) | Strand Length of Oligonucleic Acid | Yield of Oligonucleic Acid (%) |
|---|---|---|---|---|---|
| Example 1 | 8.4 | 69 | 0.65 | 49mer (RNA) | 57.8 |
| Example 2 | 8.4 | 69 | 0.7 | 49mer (RNA) | 46.2 |
| Example 3 | 8.4 | 69 | 0.7 | 49mer (RNA) | 54.9 |
| Example 4 | 8.4 | 69 | 0.79 | 49mer (RNA) | 46.2 |
| Example 5 | 5.8 | 81 | 0.71 | 49mer (RNA) | 54.5 |
| Example 6 | 7.7 | 78 | 1.03 | 103mer (RNA) | 38.1 |
| Example 7 | 9.9 | 80 | 0.49 | 103mer (RNA) | 31.6 |
| Example 8 | 13.8 | 81 | 0.48 | 49mer (RNA) | 42.8 |
| Example 9 | 15.1 | 86 | 0.57 | 49mer (RNA) | 50.5 |
| Example 10 | 8.4 | 69 | 0.87 | 49mer (RNA) | 60.4 |
| Example 11 | 3.9 | 85 | 1.09 | 49mer (RNA) | 44.6 |
| Comparative Example 1 | 8.4 | 69 | 0.68 | 49mer (RNA) | 39.2 |
| Comparative Example 2 | 8.4 | 69 | 0.77 | 49mer (RNA) | 39.2 |
| Comparative Example 3 | 5.8 | 81 | 0.99 | 49mer (RNA) | 48.2 |
| Comparative Example 4 | 7.7 | 78 | 1.14 | 103mer (RNA) | 32.4 |
| Comparative Example 5 | 3.9 | 85 | 0.79 | 49mer (RNA) | 33.2 |

According to the results shown in Table 1, it is possible to confirm that the yield of oligonucleic acid is higher in the case of use of the solid-phase carriers of Examples 1 to 4 and 10 than in the case of use of the solid-phase carriers of Comparative Examples 1 and 2.

It is possible to confirm that the yield of oligonucleic acid is higher in the case of use of the solid-phase carrier of Example 5 than in the case of use of the solid-phase carrier of Comparative Example 3.

It is possible to confirm that the yield of oligonucleic acid is higher in the case of use of the solid-phase carrier of Example 6 than in the case of use of the solid-phase carrier of Comparative Example 4.

It is possible to confirm that the yield of oligonucleic acid is higher in the case of use of the solid-phase carrier of Example 11 than in the case of use of the solid-phase carrier of Comparative Example 5.

[Measurement of Oligonucleic Acid Purity]

The solution prepared from the resulting crude oligonucleotide (each of Examples 6 and 7 and Comparative Example 4) were separated into each of ingredients by high performance liquid chromatography HPLC (wavelength 260 nm, column DNAPac™ PA100 4×250 mm). The peak width defined as "10% width", which meant the width at the 10% height of the LC peak top height of the main product according to the measured chromatogram, was determined. The results are shown in Table 2.

Here, when the purity of the oligonucleic acid is high, the "10% width" has a small value, and when the purity of the oligonucleic acid is low, the "10% width" has a large value.

TABLE 2

| | Inorganic Porous Carrier represented by General Formula (1) | | | | Pore Size mode diameter (μm) | Particle Size median diameter (μm) | Pore Volume per Volume (mL/mL) |
|---|---|---|---|---|---|---|---|
| | Inorganic Porous Substance | Substance | $R^1$, $R^2$ | L | | | |
| Example 6 | SP (3) | Zeolite | Isopropyl Group | $CH_2$ | 0.11 | 48 | 0.34 |
| Example 7 | SP (4) | Zeolite | Isopropyl Group | $CH_2$ | 0.16 | 68 | 0.27 |
| Comparative Example 4 | SP (3) | Zeolite | Ethoxy Group | $CH_2$ | 0.11 | 48 | 0.34 |

| | Surface Area per Volume ($m^2$/mL) | Porosity (%) | Density of Grafted Nucleoside (μmol/$m^2$) | Strand Length of Oligonucleic Acid | 10% width of Oligonucleic Acid |
|---|---|---|---|---|---|
| Example 6 | 7.7 | 77 | 1.03 | 103mer (RNA) | 0.34 |
| Example 7 | 9.9 | 80 | 0.49 | 103mer (RNA) | 0.38 |
| Comparative Example 4 | 7.7 | 77 | 1.14 | 103mer (RNA) | 0.78 |

According to the results shown in Table 2, it is possible to confirm that the purity of the oligonucleic acid is higher in the case of use of the solid-phase carriers of Examples 6 to 7 than in the case of use of the solid-phase carriers of Comparative Example 4.

As a result, it is possible to conclude that the yield and purity can be further improved in the preparation of oligonucleic acid when the solid-phase carrier of the present invention is used.

INDUSTRIAL APPLICABILITY

The present invention provides a method for preparing nucleic acid, which can improve the yield and purity even in the synthesis of long-stranded nucleic acid. The nucleic acid obtained by the preparation method with the inorganic porous carrier according to the present invention is useful as a raw material for pharmaceutical products.

Sequence Listing Free Text

SEQ ID NOs: 1 to 3 in the sequence listing represent the base sequences of oligonucleotides prepared according to the preparation method of the present invention.

Sequence Listing

The invention claimed is:

1. An inorganic porous carrier, comprising:
an inorganic porous substance and a linker bonded to the inorganic porous substance and represented by the following formula (1), wherein the inorganic porous substance has a pore distribution in which a pore size, which is a mode diameter, is at least 0.04 μm:

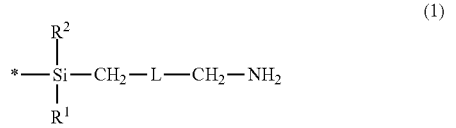

(1)

wherein, * represents a bond to an oxygen atom of a silanol group in the inorganic porous substance;
$R^1$ and $R^2$ represent each independently an alkyl group comprising 3 to 10 carbon atoms optionally substituted with a substituent selected from the group consisting of an alkoxy group and a fluorine atom; or a phenyl group optionally substituted with a substituent selected from the group consisting of an alkyl group, an alkoxy group and a fluorine atom; and
L represents a single bond; an alkylene group containing 1 to 20 carbon atoms; or an alkylene group containing 2 to 20 carbon atoms which contains —CH$_2$-Q-CH$_2$— group wherein any group Q selected from a group consisting of —O—, —NH—, —NH—CO— and —NH—CO—NH— is inserted into at least one of —CH$_2$—CH$_2$— group constituting the alkylene group; providing that a carbon atom of a methylene group bound to the group Q does not bond to another group Q at the same time.

2. The inorganic porous carrier according to claim 1, wherein a surface area per volume of the inorganic porous substance is from 0.1 m$^2$/mL to 100 m$^2$/mL.

3. The inorganic porous carrier according to claim 1, wherein a pore volume per volume of the inorganic porous substance is from 0.05 mL/mL to 0.6 mL/mL.

4. The inorganic porous carrier according to claim 1, wherein the inorganic porous substance has a porosity of at least 50%.

5. The inorganic porous carrier according to claim 1, wherein the inorganic porous substance has a particle size, which is a median diameter, of from 1 μm to 1000 μm.

6. The inorganic porous carrier according to claim 1, wherein the inorganic porous substance is silica, silica gel, zeolite, or glass.

7. An inorganic porous carrier, comprising:
an inorganic porous substance and a linker bonded to the inorganic porous substance and represented by the following formula (2), wherein the inorganic porous substance has a pore distribution in which a pore size, which is a mode diameter, is at least 0.04 μm:

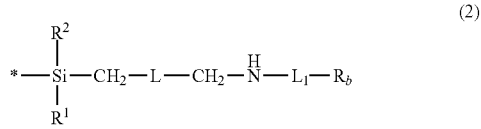

(2)

wherein * represents a bond to an oxygen atom of a silanol group in the inorganic porous substance;
$R^1$ and $R^2$ represent each independently an alkyl group comprising 3 to 10 carbon atoms optionally substituted with a substituent selected from the group consisting of an alkoxy group and a fluorine atom; or a phenyl group optionally substituted with a substituent selected from the group consisting of an alkyl group, an alkoxy group and a fluorine atom;
L represents a single bond; an alkylene group comprising 1 to 20 carbon atoms; or an alkylene group comprising 2 to 20 carbon atoms which comprises —CH$_2$-Q-CH$_2$— group wherein the group Q selected from the group consisting of —O—, —NH—, —NH—CO— and —NH—CO—NH— is inserted into at least one of —CH$_2$—CH$_2$— group constituting the alkylene group; provided that a carbon atom of a methylene group bound to the group Q does not bond to another group Q at the same time;
$R_b$ represents a nucleoside or nucleotide in which a reactive group is protected or deprotected; and
$L_1$ represents a divalent group bound to an oxygen atom of a primary or secondary hydroxyl group in $R_b$.

8. The inorganic porous carrier according to claim 7, wherein $L_1$ in the formula (2) includes a succinyl group as a functional group.

9. The inorganic porous carrier according to claim 7, wherein the linker has a density of from 0.1 μmol/m$^2$ to 5.0 μmol/m$^2$ with respect to a specific surface area per mass of the inorganic porous substance.

10. The inorganic porous carrier according to claim 7, wherein a surface area per volume of the inorganic porous substance is from 0.1 m$^2$/mL to 100 m$^2$/mL.

11. The inorganic porous carrier according to claim 7, wherein a pore volume per volume of the inorganic porous substance is from 0.05 mL/mL to 0.6 mL/mL.

12. The inorganic porous carrier according to claim 7, wherein the inorganic porous substance has a porosity of at least 50%.

13. The inorganic porous carrier according to claim 7, wherein the inorganic porous substance has a particle size, which is a median diameter, of from 1 μm to 1000 μm.

14. The inorganic porous carrier according to claim 7, wherein the inorganic porous substance is silica, silica gel, zeolite, or glass.

15. A method for preparing a nucleic acid, using an inorganic porous carrier, wherein $R_b$ in the following formula (2) represents a nucleoside or nucleotide in which a hydroxyl group as a reactive group is protected,

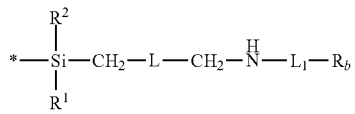

(2)

wherein * represents a bond to an oxygen atom of a silanol group in an inorganic porous substance;

$R^1$ and $R^2$ represent each independently an alkyl group comprising 3 to 10 carbon atoms optionally substituted with a substituent selected from the group consisting of an alkoxy group and a fluorine atom; or a phenyl group optionally substituted with a substituent selected from the group consisting of an alkyl group, an alkoxy group and a fluorine atom;

L represents a single bond; an alkylene group comprising 1 to 20 carbon atoms; or an alkylene group comprising 2 to 20 carbon atoms which comprises —CH$_2$-Q-CH$_2$— group wherein the group Q selected from the group consisting of —O—, —NH—, —NH—CO— and —NH—CO—NH— is inserted into at least one of —CH$_2$—CH$_2$— group constituting the alkylene group; provided that a carbon atom of a methylene group bound to the group Q does not bond to another group Q at the same time; and $L_1$ represents a divalent group bound to an oxygen atom of a primary or secondary hydroxyl group in $R_b$, the method comprising:

(A) deprotecting a protecting group of the hydroxyl group at a 5' position of the nucleoside;

(B) subjecting the hydroxyl group at the 5' position of the nucleoside produced in (A) to a condensation reaction with an amidite compound having a second nucleoside base to produce a phosphite;

(C) oxidizing the phosphite produced in (B) to produce a nucleotide; and (D) deprotecting a protecting group of a hydroxyl group at a 5' position of the nucleotide produced in (C).

16. The method according to claim 15, further comprising:

(B') subjecting a product produced in (D) to a condensation reaction with an amidite compound having a nucleoside base to produce a phosphite;

(C') oxidizing the phosphite produced in (B') to produce an oligonucleotide; and (D') deprotecting a protecting group of a hydroxyl group at a 5' position in an end of an oligonucleotide strand produced in (C').

17. The method according to claim 16, further comprising:

(E) repeating (B'), (C') and (D') m times, wherein m is an integer of 1 or more, to react a number of m of amidite compounds; and cleaving an elongated nucleic acid.

* * * * *